(12) United States Patent
Pulugurtha et al.

(10) Patent No.: US 11,992,625 B2
(45) Date of Patent: May 28, 2024

(54) CATHETER INCLUDING VARIABLE DENSITY STRUCTURAL SUPPORT MEMBER

(71) Applicant: Covidien LP, Mansfield, MA (US)

(72) Inventors: Syamala Rani Pulugurtha, Irvine, CA (US); Ujwal Jalgaonkar, Irvine, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/922,825

(22) Filed: Jul. 7, 2020

(65) Prior Publication Data
US 2022/0008692 A1    Jan. 13, 2022

(51) Int. Cl.
*A61M 25/00*    (2006.01)

(52) U.S. Cl.
CPC .... *A61M 25/0053* (2013.01); *A61M 25/0012* (2013.01); *A61M 25/0054* (2013.01); *A61M 2205/02* (2013.01)

(58) Field of Classification Search
CPC ...... A61M 2205/02; A61M 2039/0232; A61M 25/0053; A61M 25/0054; A61M 25/0012; A61M 25/01; A61M 2025/0681; A61M 25/005; A61M 25/0043; A61M 25/0102; A61M 25/0045; A61M 2025/1084
See application file for complete search history.

(56) References Cited

U.S. PATENT DOCUMENTS 5,571,073 A    11/1996    Castillo
5,891,114 A *    4/1999    Chien ............... A61M 25/0053
                                                   138/123

(Continued)

FOREIGN PATENT DOCUMENTS

EP    1092449 A1    4/2001
EP    1123714 A1    8/2001
(Continued)

OTHER PUBLICATIONS

Bhushan, "Surface Roughness Analysis and Measurement Techniques," Modern Tribology Handbook, vol. One, CRC Press, 2001, pp. 49-119, 71 pp. (year of publication is sufficiently earlier than the effective U.S. filing date so that the particular month of publication is not in issue).

(Continued)

*Primary Examiner* — Scott J Medway
(74) *Attorney, Agent, or Firm* — Shumaker & Sieffert, P.A.

(57) ABSTRACT

In some examples, a catheter includes an elongated body that includes an inner liner, and outer jacket, and a structural support member positioned between at least a portion of the inner liner and the outer jacket. The outer jacket includes a plurality of outer jacket segments in which each outer jacket segment of the plurality is longitudinally adjacent to another outer jacket segment of the plurality. The structural support member includes a first section having a first density, a second section distal to the first section and having a second density, and a third section distal to the second section and having a third density, such that the second density being higher than the first and third densities. The second section of the structural support member is longitudinally aligned with a junction between two outer jacket segments of the plurality of outer jacket segments.

17 Claims, 4 Drawing Sheets

(56) References Cited

U.S. PATENT DOCUMENTS

| | | | | |
|---|---|---|---|---|
| 5,897,537 | A * | 4/1999 | Berg | F16L 11/081 |
| | | | | 604/525 |
| 5,971,975 | A * | 10/1999 | Mills | A61M 25/0054 |
| | | | | 604/525 |
| 6,053,903 | A * | 4/2000 | Samson | A61M 25/005 |
| | | | | 604/524 |
| 6,143,013 | A * | 11/2000 | Samson | A61M 25/005 |
| | | | | 606/192 |
| 6,217,565 | B1 * | 4/2001 | Cohen | A61M 25/005 |
| | | | | 604/525 |
| 6,508,806 | B1 * | 1/2003 | Hoste | A61M 25/0012 |
| | | | | 138/124 |
| 6,511,462 | B1 | 1/2003 | Itou et al. | |
| 6,591,472 | B1 * | 7/2003 | Noone | A61M 25/0009 |
| | | | | 264/171.13 |
| 7,094,243 | B2 | 8/2006 | Mulholland et al. | |
| 7,306,585 | B2 * | 12/2007 | Ross | A61L 29/06 |
| | | | | 604/523 |
| 7,905,877 | B1 * | 3/2011 | Jimenez | A61M 25/0053 |
| | | | | 604/525 |
| 8,702,679 | B2 * | 4/2014 | Deckman | A61M 25/005 |
| | | | | 604/523 |
| 10,668,258 | B1 * | 6/2020 | Calhoun | A61M 25/0054 |
| 10,780,246 | B2 * | 9/2020 | Yao | A61M 25/0053 |
| 10,821,264 | B1 * | 11/2020 | Torres | A61M 25/0053 |
| 11,191,924 | B2 * | 12/2021 | Watanabe | A61M 25/0097 |
| 2003/0135198 | A1 * | 7/2003 | Berhow | A61M 25/005 |
| | | | | 604/524 |
| 2004/0153049 | A1 * | 8/2004 | Hewitt | A61M 25/0012 |
| | | | | 604/527 |
| 2004/0193140 | A1 * | 9/2004 | Griffin | A61M 25/0068 |
| | | | | 604/524 |
| 2005/0020974 | A1 * | 1/2005 | Noriega | A61M 25/0054 |
| | | | | 604/95.04 |
| 2006/0100602 | A1 * | 5/2006 | Klint | A61B 17/12113 |
| | | | | 604/524 |
| 2006/0200110 | A1 | 9/2006 | Lentz et al. | |
| 2010/0030165 | A1 * | 2/2010 | Takagi | A61M 25/0054 |
| | | | | 604/265 |
| 2010/0228205 | A1 | 9/2010 | Hu et al. | |
| 2011/0288532 | A1 * | 11/2011 | Faherty | A61M 25/0017 |
| | | | | 604/525 |
| 2012/0095545 | A1 * | 4/2012 | Yamagata | A61M 27/008 |
| | | | | 623/1.16 |
| 2014/0046297 | A1 * | 2/2014 | Shimada | A61M 25/10 |
| | | | | 604/508 |
| 2014/0074144 | A1 | 3/2014 | Shrivastava et al. | |
| 2016/0074621 | A1 | 3/2016 | Yao et al. | |
| 2016/0346503 | A1 * | 12/2016 | Jackson | A61M 25/0012 |
| 2017/0072163 | A1 * | 3/2017 | Lim | A61M 25/005 |
| 2017/0119409 | A1 | 5/2017 | Ma | |
| 2017/0182290 | A1 * | 6/2017 | Stern | A61M 25/0053 |
| 2018/0250498 | A1 * | 9/2018 | Stern | A61M 25/0045 |
| 2018/0289925 | A1 * | 10/2018 | Palmer | A61M 25/005 |
| 2019/0134348 | A1 * | 5/2019 | Wada | A61M 25/0054 |
| 2020/0305890 | A1 * | 10/2020 | Lorenzo | A61M 25/1006 |
| 2020/0391009 | A1 * | 12/2020 | Martin | A61M 25/005 |

FOREIGN PATENT DOCUMENTS

| | | |
|---|---|---|
| EP | 1787674 A1 | 5/2007 |
| EP | 2174685 A1 | 4/2010 |
| WO | 1998050098 A1 | 11/1998 |
| WO | 2007124500 A1 | 11/2007 |
| WO | 2017033535 A1 | 3/2017 |

OTHER PUBLICATIONS

Che et al., "Charge transfer, surface charging, and overlayer-induced faceting," Physical Review B, 67, The American Physical Society, Mar. 2003, 8 pp.

Kim et al., "Printing ferromagnetic domains for untethered fast-transforming soft materials," Letter, accessed from https://doi.org/10.1038/s41586-018-0185-0, Nature, vol. 558, Jun. 14, 2018, 18 pp.

Kovacevic et al., "Surface and Interface Phenomenon in Polymers," International Workshop on Advanced Polymer Science and Turbulent Drag Reduction, Mar. 10-20, 2008, 93 pp.

Navada, "Surface Activation to Improve Adhesion between Nitinol Wire and Polyurethane Film," Unpublished Thesis, accessed from https://repository.lib.ncsu.edu/bitstream/handle/1840.16/8216/etd.pdf?sequence=2&isAllowed=y, Aug. 9, 2012, 81 pp.

Sargeant et al., "Covalent Functionalization of NiTi Surfaces with Bioactive Peptide Amphiphile Nanofibers," Biomaterials, Mar. 29, 2008, accessed from NIH Public Access, 27 pp.

Shabalovskaya et al., "Critical overview of Nitinol surfaces and their modifications for medical applications," Acta Biomaterialia, vol. 4, Elsevier, available online Feb. 6, 2008, 21 pp.

U.S. Appl. No. 16/922,649, filed Jul. 7, 2020, naming inventors Pulugurtha et al.

Lee et al., "An evaluation of the machinability of nitinol shape memory alloy by electrochemical polishing.", Journal of mechanical science and technology, vol. 25, No. 4, Apr. 2011, pp. 963-969.

Office Action from U.S. Appl. No. 16/922,649, dated Apr. 22, 2022, 12 pp.

Response to Communication pursuant to Rule 70(1) and 70a(1), dated Jan. 24, 2022, from counterpart European Patent Application No. 21184122.6, filed May 4, 2022, 100 pp.

Extended Search Report from counterpart European Application No. 21184122.6 dated Dec. 16, 2021, 8pp.

Response to Office Action dated Apr. 22, 2022 from U.S. Appl. No. 16/922,649, filed Jul. 22, 2022, 11 pp.

Final Office Action from U.S. Appl. No. 16/922,649 dated Nov. 3, 2022, 12 pp.

Response to Final Office Action dated Nov. 3, 2022 from U.S. Appl. No. 16/922,649, filed Dec. 27, 2022, 8 pp.

Advisory Action from U.S. Appl. No. 16/922,649 dated Jan. 13, 2023, 3 pp.

Office Action from U.S. Appl. No. 16/922,649 dated Feb. 15, 2023, 14 pp.

Response to Office Action dated Feb. 15, 2023 from U.S. Appl. No. 16/922,649, filed May 12, 2023, 11 pp.

Final Office Action from U.S. Appl. No. 16/922,649 dated Aug. 21, 2023, 15 pp.

Advisory Action from U.S. Appl. No. 16/922,649 dated Nov. 15, 2023, 3 pp.

Response to Advisory Action dated Nov. 15, 2023, from U.S. Appl. No. 16/922,649, filed Nov. 20, 2023, 11 pp.

Response to Final Office Action dated Aug. 21, 2023 from U.S. Appl. No. 16/922,649, filed Oct. 23, 2023, 10 pp.

Response to Office Action dated Dec. 19, 2023 from U.S. Appl. No. 16/922,649, filed Mar. 19, 2024, 12 pp.

* cited by examiner

CATHETER INCLUDING VARIABLE DENSITY STRUCTURAL SUPPORT MEMBER

TECHNICAL FIELD

This disclosure relates to medical catheters and methods of making the same.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters with increased adhesion between a structural support member, such as a coil or braid, and an inner liner and/or outer jacket, and methods of forming catheters.

In some examples described herein, a catheter includes an inner liner, an outer jacket, and a structural support member positioned between at least a portion of the inner liner and at least a portion of the outer jacket. The outer jacket includes a plurality of outer jacket segments. Each outer jacket segment is longitudinally adjacent to another outer jacket segment, and at least two of the outer jacket segments may have different properties, such as different materials, different durometers, and/or different thicknesses. Due to the different properties of the adjacent outer jacket segments, a junction between adjacent outer jacket segments may be a relatively weak spot at which the catheter body may be more likely to buckle or kink. To reinforce the junction, the structural support member includes a variable density that is higher near the junction. For example, an intermediate section of the structural support member that is longitudinally aligned with a junction between two outer jacket segments may have a relatively high density compared to adjacent sections of the structural support member proximal and distal to the intermediate section. The relatively high density section may enable the catheter body to resist compression at the junction between the two outer jacket segments, such that the structural support member may be less likely to collapse at the junction response to compression or bending forces experienced while navigating the catheter through the vasculature compared to catheters that do not include a relatively high density section of a structural support member at a junction between two adjacent outer jacket segments.

Clause 1: In one example, a catheter includes an elongated body including an inner liner, an outer jacket including a plurality of outer jacket segments, wherein each outer jacket segment of the plurality is longitudinally adjacent to another outer jacket segment of the plurality, and a structural support member positioned between at least a portion of the inner liner and the outer jacket, wherein a first section of the structural support member has a first density, a second section of the structural support member distal to the first section has a second density, and a third section of the structural support member distal to the second section has a third density, the second density being higher than the first and third densities, wherein the second section of the structural support member is longitudinally aligned with a junction between two outer jacket segments of the plurality of outer jacket segments.

Clause 2: In some examples of the catheter of clause 1, at least two outer jacket segments of the plurality have different materials.

Clause 3: In some examples of the catheter of clause 1 or 2, at least two outer jacket segments of the plurality have different durometers.

Clause 4: In some examples of the catheter of clause 3, the plurality of outer jacket segments includes a first outer jacket segment and a second outer jacket segment distal to the first outer jacket segment, and a durometer of the first outer jacket segment is greater than a durometer of the second outer jacket segment.

Clause 5: In some examples of the catheter of clause 3, the plurality of outer jacket segments includes a first outer jacket segment and a second outer jacket segment distal to the first outer jacket segment, and a durometer of the first outer jacket segment is less than a durometer of the second outer jacket segment.

Clause 6: In some examples of the catheter of any of clauses 1-5, at least two outer jacket segments of the plurality have different thicknesses.

Clause 7: In some examples of the catheter of clause 6, the plurality of outer jacket segments includes a first outer jacket segment and a second outer jacket segment distal to the first outer jacket segment, and wherein a thickness of the first outer jacket segment is less than a thickness of the second outer jacket segment.

Clause 8: In some examples of the catheter of clause 6, the plurality of outer jacket segments includes a first outer jacket segment and a second outer jacket segment distal to the first outer jacket segment, and wherein a thickness of the first outer jacket segment is greater than a thickness of the second outer jacket segment.

Clause 9: In some examples of the catheter of any of clauses 1-8, the structural support member includes a coiled structural support member.

Clause 10: In some examples of the catheter of any of clauses 1-8, the structural support member includes a braided structural support member.

Clause 11: In some examples of the catheter of any of clauses 1-10, a surface of at least the second section of the structural support member is surface treated to increase an adhesion of the surface to at least one of the inner liner or the outer jacket.

Clause 12: In some examples of the catheter of any of clauses 1-11, the structural support member tapers from a first diameter at a proximal end of the elongated body to a second diameter at a distal end of the elongated body.

Clause 13: In some examples of the catheter of any of clauses 1-12, the first section is radially adjacent to a first outer jacket segment, the second section is radially adjacent to a second outer jacket segment having a lower durometer than the first outer jacket segment, and the third section is radially adjacent to a third outer jacket segment having a lower durometer of the first and second outer jacket segments.

Clause 14: In one example, a catheter includes an elongated body including an inner liner, an outer jacket including a plurality of outer jacket segments, wherein each outer jacket segment of the plurality is longitudinally adjacent to another outer jacket segment of the plurality, and a structural support member positioned between at least a portion of the inner liner and the outer jacket, wherein the structural support member includes one or more relatively high density sections interspersed between adjacent relatively low density sections, wherein each relatively high density section has a density at least 25% greater than the adjacent relatively low density sections, and wherein at least one relatively high density section of the one or more relatively high density sections is longitudinally aligned with a junction between two outer jacket segments of the plurality of outer jacket segments.

Clause 15: In some examples of the catheter of clause 14, at least two outer jacket segments of the plurality have different materials, different durometers, or different thicknesses.

Clause 16: In some examples of the catheter of clause 14 or 15, the at least one relatively high density section overlaps the junction by between about 5 millimeters and about 20 millimeters.

Clause 17: In some examples of the catheter of any of clauses 14-16, a durometer of the outer jacket decreases from a proximal end of the elongated body to a distal end of the elongated body.

Clause 18: In some examples of the catheter of any of clauses 14-17, a surface of at least the at least one relatively high density section of the structural support member is surface treated to increase an adhesion of the surface to at least one of the inner liner or the outer jacket.

Clause 19: In some examples of the catheter of any of claims 14-18, the structural support member tapers from a first diameter at a proximal end of the elongated body to a second diameter at a distal end of the elongated body.

Clause 20: In some examples of the catheter of any of claim 14-19, the at least one relatively high density section is radially adjacent to a first outer jacket segment, and the adjacent relatively low density sections are radially adjacent respective first and third outer jacket segments having a higher durometer than the second outer jacket segment.

Clause 21: In one example, a method for manufacturing a catheter includes positioning a structural support member around at least a portion of an inner liner, and positioning a plurality of outer jacket segments over the structural support member, wherein each outer jacket segment of the plurality is longitudinally adjacent to another outer jacket segment of the plurality, wherein a first section of the structural support member has a first density, a second section of the structural support member distal to the first section has a second density, and a third section of the structural support member distal to the second section has a third density, the second density being higher than the first and third densities, and wherein the second section of the structural support member is longitudinally aligned with a junction between two outer jacket segments of the plurality.

Clause 22: In some examples of the method of clause 21, positioning the plurality of outer jacket segments around the structural support member and the inner liner includes positioning a first sleeve corresponding to a first outer jacket segment over the structural support member and positioning a second sleeve corresponding to a second outer jacket segment over the structural support member, distal to the first sleeve.

Clause 23: In some examples of the method of clause 21 or 22, at least two outer jacket segments of the plurality have different materials.

Clause 24: In some examples of the method of any of clauses 21-23, at least two outer jacket segments of the plurality have different durometers.

Clause 25: In some examples of the method of clause 24, the plurality of outer jacket segments includes a first outer jacket segment and a second outer jacket segment distal to the first outer jacket segment, and wherein a durometer of the first outer jacket segment is greater than a durometer of the second outer jacket segment.

Clause 26: In some examples of the method of clause 24, the plurality of outer jacket segments includes a first outer jacket segment and a second outer jacket segment distal to the first outer jacket segment, and wherein a durometer of the first outer jacket segment is less than a durometer of the second outer jacket segment.

Clause 27: In some examples of the method of any of clauses 21-26, at least two outer jacket segments of the plurality have different thicknesses.

Clause 28: In some examples of the method of clause 27, the plurality of outer jacket segments includes a first outer jacket segment and a second outer jacket segment distal to the first outer jacket segment, and wherein a thickness of the first outer jacket segment is less than a thickness of the second outer jacket segment.

Clause 29: In some examples of the method of clause 27, the plurality of outer jacket segments includes a first outer jacket segment and a second outer jacket segment distal to the first outer jacket segment, and wherein a thickness of the first outer jacket segment is greater than a thickness of the second outer jacket segment.

Clause 30: In some examples of the method of any of clauses 21-29, the structural support member tapers from a first diameter at a proximal end of the elongated body to a second diameter at a distal end of the elongated body.

Clause 31: In some examples of the method of any of clauses 21-30, the structural support member includes at least one of a coiled structural support member or a braided structural support member.

Clause 32: In some examples of the method of any of clauses 21-31, the first section is adjacent to a first outer jacket segment, the second section is adjacent to a second outer jacket segment having a lower durometer than the first outer jacket segment, and the third section is adjacent to a third outer jacket segment having a lower durometer of the first and second outer jacket segments.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
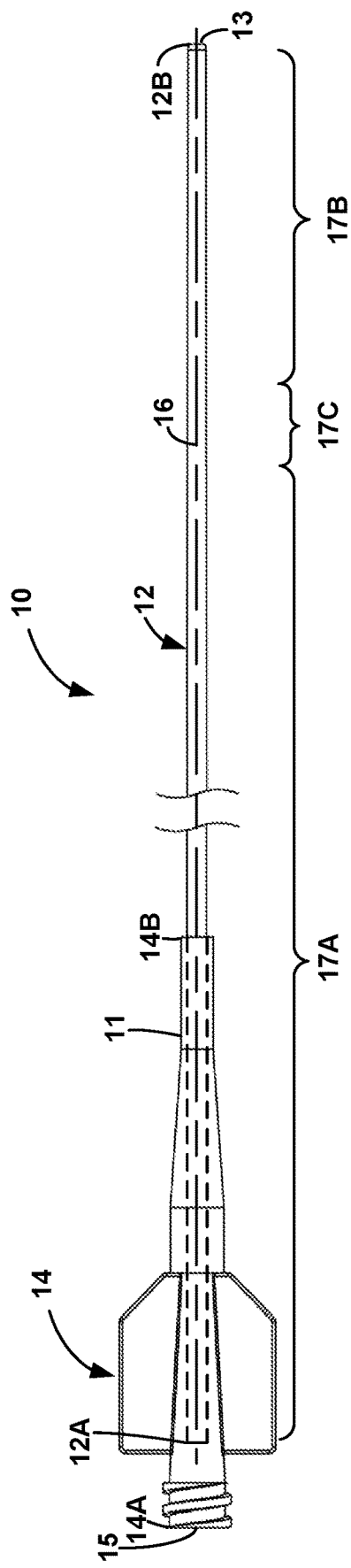
FIG. 1 is a side elevation view of an example catheter, which includes a catheter body and a hub.

The disclosure describes a catheter that includes a relatively flexible catheter body with increased structural integrity that is configured to be navigated through vasculature of a patient. Catheters may be used to diagnose and treat a variety of conditions, including thrombosis. For example, thrombosis occurs when a thrombus (e.g., a blood clot or other embolus) forms and obstructs vasculature of a patient. In some medical procedures, to treat a patient with thrombosis, a clinician may position an aspiration catheter in a blood vessel of the patient (i.e., catheterization) near the thrombus, apply suction to the aspiration catheter, and engage the thrombus with a tip of the aspiration catheter. This medical procedure may be, for example, A Direct Aspiration first Pass Technique (ADAPT) for acute stroke thrombectomy, or any other aspiration of thrombus or other material from the neurovasculature or other blood vessels.

In addition to or instead of medical aspiration, a catheter can be used to deliver a therapeutic device to a target treatment site within vasculature (e.g., neurovasculature) of a patient to treat a defect in the vasculature, such as, but not limited to, aneurysms or arteriovenous malformations. The therapeutic neurovascular device may include any suitable medical device configured to be used to treat a defect in vasculature of a patient or used to facilitate treatment of the neurovasculature. For example, the therapeutic device can include a thrombectomy device, a flow diverter, a stent, an aspiration catheter, a drug delivery catheter, a balloon catheter, a microvascular plug, a filter, an embolic retrieval device (e.g., a stent retriever or an aspiration catheter), or an implantable medical device, such as an embolic coil.

To position a catheter in a blood vessel of a patient, a clinician may push a proximal portion (e.g., a proximal end) of the catheter to advance the catheter through the blood vessel. Walls of the blood vessel may guide a distal tip (e.g., at a distal end) of the catheter through the blood vessel. However, some blood vessels, such as cerebral arteries, have tortuous configurations. These tortuous configurations may include relatively low radius bends that sharply bend the catheter or create resistance along a longitudinal axis of the catheter. As discussed in further detail below, the catheters described herein enable the catheter to be navigated to a target site within vasculature of a patient with relatively high structural integrity e.g., by increasing adhesion between the structural support member and the outer jacket and/or inner liner and/or by supporting transitions in a segmented outer jacket using an increased density (e.g., pitch or braid density, which can be expressed in pics per inch) of the structural support member. As a result, the catheters described herein may stabilize (e.g., resist delamination between) the structural support member and the outer jacket and/or inner liner and/or resist buckling in the segmented outer jacket.

In some examples described herein, a catheter includes a structural support member positioned between an inner liner and an outer jacket. Prior to or during assembly of the catheter, the structural support member can be surface treated by applying a surface treatment to the overall surface or to at least a portion of the structural support member, such as an inner and/or outer radial surface. Some surface treatments can include physical treatments, such as roughening, to increase a roughness and/or surface area of the structural support member in contact with the outer jacket, inner liner, and/or a support layer. Some surface treatments can include chemical treatments, such as functionalization or coatings, to increase a charge or generate reactive moieties on the structural support member to bond with outer jacket, inner liner, and/or a support layer. The surface-treated structural support member may more strongly and/or readily adhere to the outer jacket and/or inner liner, either directly or through an intermediate support layer, such that the structural support member may be less likely to separate from the outer jacket and/or inner liner in response to compression or bending forces experienced while navigating the catheter through the vasculature compared to catheters that do not include a surface treated structural support member.

In some examples, the surface treatment can be applied to, or in various amount at, particular portions of the structural support member to increase the adhesion between the particular portions of the structural support member and the inner liner and/or outer jacket. Certain portions of the structural support member may be more likely to experience separation from the inner liner and/or outer jacket than other portions of the catheter, such as due to relatively higher forces or deformation experienced at these portions or reduced inter-coil or inter-braid contact between the inner liner and outer jacket at these portions. For example, during formation of the outer jacket, a higher density or diameter section of the structural support member may reduce flow of an outer jacket material between structures (e.g., coils) of the structural support member (e.g., during heat shrinking of the outer jacket material or during a reflow process). This reduced flow may result in reduced contact between the inner liner and the outer jacket, whether directly (as in a tri-layer catheter design) or via a support layer (as in a quad-layer catheter design). The structural support member may be surface treated to at least partly compensate for a smaller contact area between the inner liner and the outer jacket.

In examples described herein, a catheter includes an inner liner, an outer jacket that includes a plurality of outer jacket segments, and a structural support member positioned between at least a portion of the inner liner and the outer jacket. Each outer jacket segment is longitudinally adjacent to another outer jacket segment, and may have different compositions or properties, such as different materials (e.g., different chemical compositions), different durometers, and/or different thicknesses. Due to structural discontinuities and/or different compositions or properties of the adjacent outer jacket segments, a junction between adjacent outer jacket segments may be a relatively weak spot at which buckling or collapse of the catheter may be more likely to occur. To reinforce the junction, the structural support member has a variable density that is relatively high (e.g., a higher coil pitch or more pics per inch in the case of a braid) near the junction compared to a density at other portions of the structural support member. For example, an intermediate section of the structural support member that is longitudinally aligned with a junction between two outer jacket segments may have a relatively high density compared to adjacent sections of the structural support member proximal and distal to the intermediate section. The relatively high density section may resist compression at the junction between the two outer jacket segments, such that the structural support member may be less likely to kink or collapse at the junction in response to compression or bending forces experienced while navigating the catheter through the vasculature compared to catheters that do not include a relatively high density section of a structural support member at a junction between two adjacent outer jacket segments.

In various ways described herein, example catheters may resist temporary (e.g., buckling) or permanent (e.g., delamination) deformation when being navigated through vasculature having tortuous configurations. FIG. 1 is a side elevation view of an example catheter 10, which includes catheter body 12 and hub 14. Catheter hub 14 is positioned at a proximal end of catheter 10 and defines an opening through which an inner lumen 26 (shown in FIG. 2) of catheter body 12 may be accessed and, in some examples, closed. For example, catheter hub 14 may include a luer connector for connecting to another device, a hemostasis valve, or another mechanism or combination of mechanisms. In some examples, catheter 10 includes strain relief member 11, which may be a part of hub 14 or may be separate from hub 14. In other examples, the proximal end of catheter 10 can include another structure in addition or, or instead of, hub 14.

Catheter body 12 is an elongated body that extends from proximal end 12A to distal end 12B and defines at least one inner lumen 26 (e.g., one inner lumen, two inner lumens, or three inner lumens) that terminates at distal opening 13 defined by catheter body 12. In the example shown in FIG. 1, proximal end 12A of catheter body 12 is received within hub 14 and is mechanically or otherwise connected to hub 14 via an adhesive, welding, or another suitable technique or combination of techniques. Opening 15 defined by hub 14 and located at proximal end 14A of hub 14 is aligned with inner lumen 26 of catheter body 12, such that inner lumen 26 of catheter body 12 may be accessed via opening 15.

Catheter body 12 has a suitable length for accessing a target tissue site within the patient from a vascular access point. The length may be measured along longitudinal axis 16 of catheter body 12. The target tissue site may depend on the medical procedure for which catheter 10 is used. For example, if catheter 10 is a distal access catheter used to access vasculature in a brain of a patient from a femoral artery access point at the groin of the patient, catheter body 12 may have a length of about 129 centimeters (cm) to about 135 cm, such as about 132 cm, although other lengths may be used. In other examples, such as examples in which catheter 10 is a distal access catheter used to access vasculature in a brain of a patient from a radial artery access point, catheter body 12 may have a length of about 80 cm to about 120 cm, such as about 85 cm, 90 cm, 95 cm, 100 cm, 105 cm, although other lengths may be used (e.g., sheaths or radial intermediate catheters may be 5-8 cm longer).

Catheter body 12 can be relatively thin-walled, such that it defines a relatively large inner diameter for a given outer diameter, which may further contribute to the flexibility and kink-resistance of catheter body 12. The wall thickness of catheter body 12 may be the difference between the outer diameter of catheter body 12 and the inner diameter of catheter body 12, as defined by inner lumen 26. For example, in some examples, an outer diameter of catheter body 12 may be about 4 French to about 12 French, such as about 5 French or about 6 French. The measurement term French, abbreviated Fr or F, is three times the diameter of a device as measured in mm. Thus, a 6 French diameter is about 2 millimeters (mm), a 5 French diameter is about 1.67 mm, a 4 French diameter is about 1.33 mm, and a 3 French diameter is about 1 mm. The term "about" or "approximately" as used herein with dimensions may refer to the exact numerical value or a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

In some examples, rather than being formed from two or more discrete and separate longitudinally extending segments that are mechanically connected to each other, e.g., at axial butt joints, catheter body 12 may be substantially continuous along a length of catheter body 12. For example, catheter body 12 may include an inner liner that defines the inner lumen 26 of catheter body 12 and continuously extends from proximal end 12A to distal end 12B of catheter body 12, and a structural support member that extends across at least a part of the proximal portion 17A, at least part of the distal portion 17B, and the medial portion 17C of catheter body 12. A substantially continuous catheter body 12 may be configured to better distribute forces in a longitudinal direction (in a direction along longitudinal axis 16) and rotational direction (rotation about longitudinal axis 16) compared to a catheter body including two or more longitudinally extending segments that are mechanically connected to each other. Thus, the substantially continuous construction of catheter body 12 may contribute to the ability of body 12 to transfer axial pushing forces from a proximal portion 17A of catheter body 12 to a distal portion 17B, as well transfer rotational forces (if any) applied from proximal portion 17A of catheter body 12 to distal portion 17B. While in some examples, as will be described with reference to FIGS. 3 and 4, catheter body 12 includes an outer jacket formed from two or more longitudinally extending segments that are in an abutting relationship, due to the continuous inner liner and the structural support member that extends along a majority of the length of catheter body 12, catheter body 12 may still better distribute forces and flexibility compared to a catheter body including two or more longitudinal sections that are mechanically connected to each other.

In some examples, at least a portion of an outer surface of catheter body 12 includes one or more coatings, such as, but not limited to, an anti-thrombogenic coating, which may help reduce the formation of thrombi in vitro, an anti-microbial coating, and/or a lubricating coating. The lubricating coating may be configured to reduce static friction and/kinetic friction between catheter body 12 and tissue of the patient as catheter body 12 is advanced through the vasculature. The lubricating coating can be, for example, a hydrophilic coating. In some examples, the entire working length of catheter body 12 (from distal end 14B of hub 14 to distal end 12B) is coated with the hydrophilic coating. In other examples, only a portion of the working length of catheter body 12 coated with the hydrophilic coating. This may provide a length of catheter body 12 distal to distal end 14B of hub 14 with which the clinician may grip catheter body 12, e.g., to rotate catheter body 12 or push catheter body 12 through vasculature.

As described in further detail below, catheter body 12 may be used to access relatively distal locations in a patient, such as the MCA in a brain of a patient. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists and/or turns) through the vasculature to reach these tissue sites. Catheter body 12 may be structurally configured to be relatively flexible, pushable, and kink-, buckle-, and delamination-resistant, so that it may resist buckling when a pushing force is applied to a relatively proximal portion of catheter 10 to advance the catheter body 12 distally through vasculature, resist kinking when traversing around a tight turn in the vasculature, and/or so resist delamination and/or layer separation when bending around a tight turn of the vasculature. As one example, kinking or buckling may occur when a weak point of a catheter body, such as a transition between different structures or materials, undergoes deformation along (e.g., buckling) or away from (e.g., kinking) in response to a bending or compressive force. As another example, delamination may occur when two or more components within a catheter body, such as an inner liner, an outer jacket, a structural support member, and/or a support layer between any of the inner liner, outer jacket, or structural support member, separate in response to a bending or compressive force. Kinking, buckling, and/or delamination of catheter body 12 may hinder a clinician's efforts to push the catheter body distally, e.g., past a turn.

A characteristic that may contribute to at least the pushability, flexibility, and/or integrity of catheter body 12 is an adhesion between the structural support member and either or both the outer jacket and the inner liner. A surface of at least a portion of the structural support member can be surface treated to increase an adhesion of the surface to at least one of the inner liner or the outer jacket, such as directly or via a support layer. In some examples, the surface treatment may include physical treatments, such as roughening the surface of a portion of the structural support member to increase a surface roughness of the surface; chemical treatments, such as chemically treating the surface of a portion of the structural support member to increase a charge of the surface or to functionalize the surface with reactive moieties; and coating treatments, such as coating the surface of a portion of the structural support member with a functional layer, such as a reactive layer with reactive moieties. The surface-treated portion of the structural support member may more readily and/or strongly adhere to the inner liner, outer jacket, and/or support layer, thereby increasing stability of the structural support member between the inner liner and the outer jacket and resisting separation due to compression or bending. This increased adhesion may be particularly useful for portions of the structural support member that correspond to sections of the inner liner or outer jacket that may not be as firmly adhered. For example, a higher density section of a variable density structural support member may have reduced surface contact between the inner liner and the outer jacket due to lower penetration of the outer jacket material or an intermediate layer (e.g., a tie layer) between the coils or braids of the structural support member.

Another characteristic that may contribute to at least the pushability, flexibility, and/or integrity of catheter body 12 is a variable density of the structural support member in relation to the longitudinally extending segments of the outer jacket. For example, the outer jacket may include a plurality of outer jacket segments in which each outer jacket segment of the plurality is longitudinally adjacent to another outer jacket segment of the plurality. A junction between two outer jacket segments may be a relatively weak point that is more susceptible to collapse in response to a longitudinal force, such as may be experienced when a catheter is pushed. The structural support member may have an increased density near the junction to support and reinforce the junction. For example, a first section of the structural support member may have a relatively low density, a second section of the structural support member distal to the first section may have a relatively high density, and a third section of the structural support member distal to the second section may have a relatively low density. To reinforce the junction between two outer jacket segments, the second, higher density section of the structural support member may be longitudinally aligned with the junction. While the junction may have reduced resistance to compression than the adjacent sections of the outer jacket, the higher density section of the structural support member may have increased resistance to compression to reduce buckling and/or kinking at the junction.

Another characteristic that may contribute to at least the pushability, flexibility, and/or integrity of catheter body 12 is a variable diameter of the structural support member and variable properties of the outer jacket. For example, a distal portion of the coiled structural support member may have a smaller diameter than a proximal portion of the coiled structural support member. This smaller diameter distal section may have increased flexibility and may enable a thicker outer jacket having a lower durometer, and therefore more flexible, material, while also enabling the catheter to maintain a relatively constant inner diameter of the inner liner and outer diameter of the outer jacket.

Any of the characteristics described herein that may contribute to at least the pushability, flexibility, and/or integrity of catheter body 12 may be used alone or in combination with each other.

Figure 2:
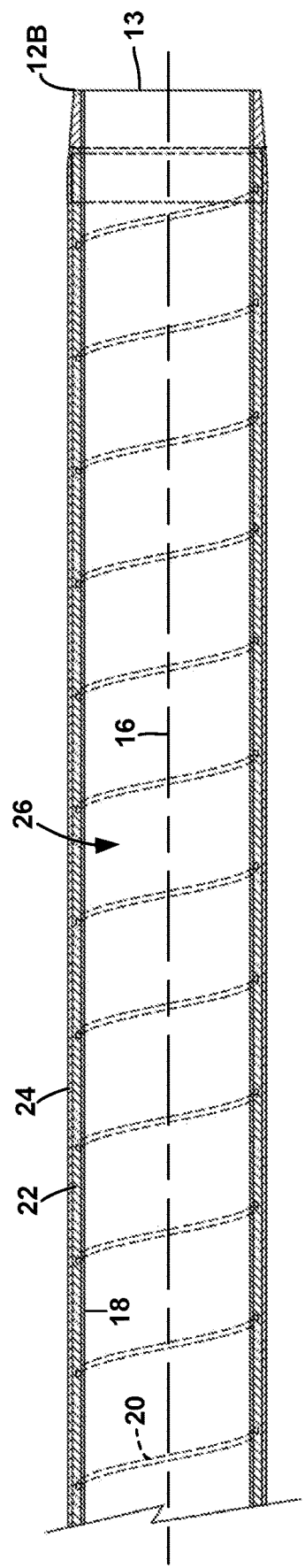
FIG. 2 is a conceptual cross-sectional view of a part of the catheter body of FIG. 1, where the cross-section is taken through a center of the catheter body and along a longitudinal axis of the catheter body.
Figure 3:
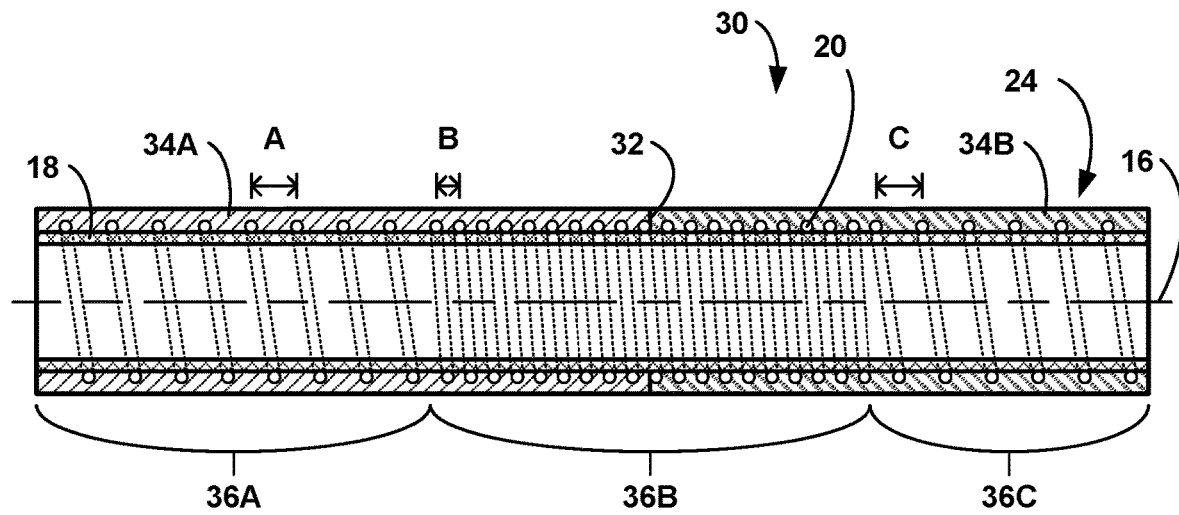
FIG. 3 is a conceptual cross-sectional view of a part of a catheter body including a coiled structural support member, where the cross-section is taken through a center of the catheter body and along a longitudinal axis of the catheter body.
Figure 4:
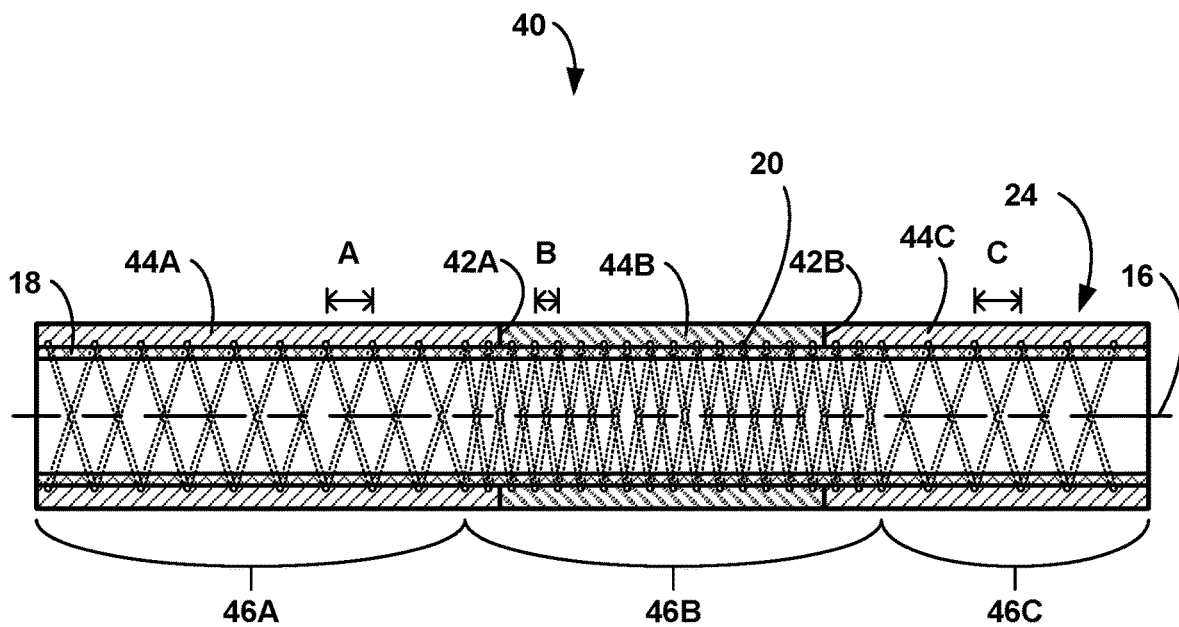
FIG. 4 is a conceptual cross-sectional view of a part of a catheter body including a braided structural support member, where the cross-section is taken through a center of the catheter body and along a longitudinal axis of the catheter body.

FIG. 2 is a conceptual cross-sectional view of a part of catheter body 12 including distal end 12B, where the cross-section is taken through a center of catheter body 12 along longitudinal axis 16. As illustrated in the quad-layer configuration of FIG. 2, catheter body 12 includes inner liner 18, structural support member 20, support layer 22, and outer jacket 24; however, in other examples, catheter body 12 may not include support layer 22, such as in a tri-layer configuration as illustrated in FIGS. 3 and 4.

Inner liner 18 defines inner lumen 26 of catheter body 12, inner lumen 26 extending from proximal end 12A to distal end 12B and defining a passageway extending from proximal end 12A to distal opening 13 at distal end 12B of catheter body 12. Inner lumen 26 may be sized to receive a medical device (e.g., another catheter, a guidewire, an embolic protection device, a stent, or any combination thereof), a therapeutic agent, or the like. At least the inner surface of inner liner 18 defining inner lumen 26 may be lubricious in some examples in order to facilitate the introduction and passage of a device, a therapeutic agent, or the like, through inner lumen 26. For example, the material from which the entire inner liner 18 is formed may be lubricious, or inner liner 18 may be formed from two or more materials, where the material that defines inner lumen 26 may be more lubricious than the material that interfaces with structural support member 20 and support layer 22. In addition to, or instead of, being formed from a lubricious material, in some examples, an inner surface of inner liner 18 is coated with a lubricious coating. Example materials from which inner liner 18 may be formed include, but are not limited to, polytetrafluoroethylene (PTFE), fluoropolymer, perfluoroalkyoxy alkane (PFA), fluorinated ethylene propylene (FEP), or any combination thereof. For example, inner liner 18 may be formed from an etched PTFE, e.g., may consist essentially of an etched PTFE.

Outer jacket 24 is positioned radially outward of inner liner 18 and structural support member 20, and, in some examples, defines an outer surface of catheter body 12. Although a coating or another material may be applied over the outer surface of outer jacket 24, outer jacket 24 may substantially define a shape and size of the outer surface of catheter body 12. Outer jacket 24, together with structural support member 20 and inner liner 18, may be configured to define catheter body 12 having the desired flexibility, kink resistance, and pushability characteristics. Outer jacket 24 may have stiffness characteristics that contribute to the desired stiffness profile of catheter body 12. For example, outer jacket 24 may be formed to have a stiffness that decreases from a proximal portion 17A of catheter body 12 to a distal portion 17B. In some examples, outer jacket 24 may be formed from two or more different materials that enable outer jacket 24 to exhibit the desired stiffness characteristics, such as may described further in FIGS. 3 and 4 below.

Structural support member 20 is configured to increase the structural integrity of catheter body 12 while allowing catheter body 12 to remain relatively flexible. For example, structural support member 20 may be configured to help catheter body 12 substantially maintain its cross-sectional shape or at least help prevent catheter body 12 from buckling or kinking as it is navigated through tortuous anatomy. Structural support member 20, together with inner liner 18, outer jacket 24, and optionally support layer 22, may help distribute both pushing and rotational forces along a length of catheter body 12, which may help prevent kinking of body 12 upon rotation of body 12 or help prevent buckling of body 12 upon application of a pushing force to body 12. As a result, a clinician may apply pushing forces, rotational forces, or both, to proximal portion 17A of catheter body 12, and such forces may cause distal portion 17B of catheter body 12 to advance distally, rotate, or both, respectively. In the example shown in FIG. 2, structural support member 20 extends along only a portion of a length of catheter body 12; however, in other examples, structural support member 20 may extend along an entire length of catheter body 12.

In some examples, structural support member 20 includes a generally tubular braided structure (e.g., as illustrated by portion 40 of catheter body 12 in FIG. 4), a coil member defining a plurality of turns (e.g., as illustrated by portion 30 of catheter body 12 in FIG. 3), or a combination of a braided structure and a coil member. Thus, although examples of the disclosure may describe structural support member 20 as a coil, in some other examples, the catheter bodies described herein may include a braided structure instead of a coil or a braided structure in addition to a coil. For example, a proximal portion of structural support member 20 may include a braided structure and a distal portion of structural support member 20 may include a coil member, or vice versa. Structural support member 20 can be made from any suitable material, such as, but not limited to, a metal (e.g., a nickel titanium alloy, stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 20 may include one or more metal wires braided or coiled around inner liner 18. The metal wires may include round wires, flat-round wires, flat wires, or any combination thereof.

Structural support member 20 may be coupled, adhered, and/or mechanically connected to at least a portion of an outer surface of inner liner 18 and/or at least a portion of an inner surface of outer jacket 24. In some examples, structural support member 20 may be directly coupled, adhered, and/or mechanically connected to at least a portion of an outer surface of inner liner 18 and/or at least a portion of an inner surface of outer jacket 24. For example, while catheter 10 of FIG. 2 illustrates a quad-layer configuration that includes support layer 22, in some examples, such as illustrated in portion 30 of FIG. 3 or portion 40 of FIG. 4, catheter 10 may include a tri-layer configuration that does not include support layer 22. In such examples, the inner surface of outer jacket 24 and the outer surface of inner liner 18 may, at least partly, directly contact and/or adhere to each other between braids or coils of structural support member 20.

In other examples, such as illustrated in FIG. 2, structural support member 20 may be indirectly coupled, adhered, and/or mechanically connected to at least a portion of the outer surface of inner liner 18 and/or at least a portion of the inner surface of outer jacket 24 via support layer 22. For example, support layer 22 may be a thermoplastic material or a thermoset material, such as a thermoset polymer and/or a thermoset adhesive. In some examples, support layer 22 is positioned between the entire length of structural support member 20 and inner liner 18, while in other examples, support layer 22 is only positioned between a part of the length of structural support member 20 and inner liner 18.

In example catheters that do not include support layer 22, such as illustrated in FIGS. 3 and 4, outer jacket 24 may be configured to fill at least part of the spaces (e.g., part or all of the spaces) between portions of structural support member 20, e.g., the spaces between turns of structural support member 20 in examples in which member 20 is a coil member or the spaces defined between pics of a braid. In example catheters that include support layer 22, support layer 22 may be configured to fill at least part of the spaces between portions of structural support member 20.

In some instances, the presence of outer jacket 24 and/or support layer 22 between turns of member 20 may help adhere outer jacket 24 and inner liner 18 to each other and securely integrate structural support member 20 into catheter body 12, such that structural support member 20 may resist detachment during bending or compression of catheter 10. For example, at least by minimizing or even eliminating voids between turns of structural support member 20, such as may be caused by insufficient flow of a material of outer jacket 24, outer jacket 24 and/or support layer 22 may provide a higher contact surface between inner liner 18 and outer jacket 24, which may better distribute pushing or torqueing forces applied to proximal portion 17A of catheter body 12 to distal portion 17B. In addition or instead, minimizing or even eliminating voids between turns of structural support member 20 may provide longitudinal support to structural support member 20 to secure structural support member within catheter body 12.

In some instances, the presence of outer jacket 24 and/or support layer 22 between turns of member 20 may help distribute the flexibility provided by member 20 along the length of member 20, which may help prevent catheter body 12 from kinking. For example, at least by eliminating voids between turns of structural support member 20, outer jacket 24 and/or support layer 22 may transfer the flexing motion from structural support member 20 along a length of catheter body 12. In some examples, support layer 22 has a thickness (measured in a direction orthogonal to longitudinal axis 16) that is greater than or equal to a cross-sectional dimension of the wire that forms the member 20, such that layer 22 is at least partially positioned between outer jacket 24 and structural support member 20. In other examples, support layer 22 has a thickness that is less than or equal to a cross-sectional dimension of the wire that forms the structural support member 20, such that support layer 22 is not positioned between outer jacket 24 and structural support member 20.

In some examples, to increase adhesion of structural support member 20 to inner liner 18 and/or outer jacket 24, a surface of at least a portion of structural support member 20 is surface treated. A surface of structural support member 20 that has been surface treated may include enhanced surface properties, such as roughness, charge, or reactive moieties. These surfaces of structural support member 20 may more strongly or readily adhere to inner liner 18, support layer 22, and/or outer jacket 24 compared to surface properties of a similar, but untreated, structural support member. As a result, structural support member 20 may be better integrated into catheter body 12 and less likely to displace in response to compressive or bending forces on catheter 10.

Increased adhesion of structural support member 20 to inner liner 18, outer jacket 24, and/or support layer 22 may be measured and/or quantified in one or more of a variety of ways including, but not limited to, shear strength (e.g., structural support member 20 detaching from inner liner 18 and/or outer jacket 24 along longitudinal axis 16), peel strength (e.g., structural support member 20 detaching from inner liner 18 and/or outer jacket 24 radially from longitudinal axis 16), and the like. In some examples, structural support member 20 and inner liner 18 and/or outer jacket 24 may have increased shear strength compared to a structural support member that does not include a surface treatment. In some examples, a shear strength of structural support member 20 may be greater than or equal to about twice a shear strength of a similar structural support member that does not include the surface treatment.

In some examples, the surface treatment may include a physical treatment. A physical treatment includes any treatment that results in an increase in contact area of the surface of structural support member 20 for bonding with inner layer 18, outer jacket 24, and/or support layer 22, or an increase in mechanical interlocking between the surface of structural support member 20 and inner liner 18, outer jacket 24, and/or support layer 22. For example, a physical treatment may increase a surface area or surface deviation (e.g., slope angle) of the surface of structural support member 20. Example physical treatments that may be used include, but are not limited to, mechanical roughening, laser roughening, abrasion, or the like, and combinations thereof.

In some examples, the surface treatment may include roughening the surface of a portion of structural support member 20, such that the portion of structural support member 20 may have an increased surface roughness of the surface. An increased surface roughness may be, for example, an increased contact area, contact slope, and/or fractality of the surface of structural support member 20 with inner liner 18, outer jacket 24, and/or support layer 22, thereby increasing adhesion between structural support member 20 and inner liner 18, outer jacket 24, and/or support layer 22. In some examples, the surface of at least a portion of the structural support member 20 includes a surface roughness greater than about 2 microns Ra (arithmetical mean deviation of profile) and/or about 100 microns Rz (maximum height of profile).

In some examples, the surface treatment may include a chemical treatment. A chemical treatment includes any treatment that results in an increase in chemical bonding between structural support member 20 and inner liner 18, outer jacket 24, and/or support layer 22. For example, a chemical treatment may increase a charge or reactivity of the surface of structural support member 20 to increase intermolecular forces (e.g., Van Der Waals forces, hydrogen bonding, ionic bonding, and/or covalent bonding) between structural support member 20 and inner liner 18, outer jacket 24, and/or support layer 22. One or more of a variety of chemical treatments may be used including, but not limited to, alkaline treatment, acid treatment, ionization, protonation, deprotonation, electric field charge, or the like, and combinations thereof.

In some examples, the surface treatment may include chemically treating the surface of a portion of structural support member 20, such that the portion of structural support member 20 may have an increased charge at the surface. An increased charge of the surface may be opposite to a charge of inner liner 18, outer jacket 24, and/or support layer 22, thereby increasing an electrostatic attraction between structural support member 20 and inner liner 18, outer jacket 24, and/or support layer 22. For example, structural support member 20 may include a positive charge, while outer jacket 24 may include a negative charge, such that structural support member 20 and outer jacket 24 may be electrostatically attracted to each other.

In some examples, the surface treatment may include chemically treating the surface of a portion of structural support member 20, such that the portion of structural support member may be functionalized with reactive moieties. For example, the surface of structural support member 20 may be reacted with an acid or base to create reactive moieties, such as amines, carboxylic acids, or other reactive groups configured to react with polymers. Inner liner 18, outer jacket 24, and/or support layer 22 may include polymers that include various functional groups capable of reacting with the reactive moieties on structural support member 20. Reactive moieties on the structural support layer may bond (e.g., covalently) with the functional groups of inner liner 18, outer jacket 24, and/or support layer 22. As a result, the surface of at least the portion of structural support member 20 may be covalently bonded to at least one of inner liner 18 or outer jacket 24.

In some examples, the surface treatment may include coating treatments, such as coating the surface of a portion of structural support member 20 with a functional layer, such as a reactive layer with reactive moieties. Rather than provide surface properties through a direct surface treatment of structural support member 20, a functional layer may provide the roughness, charge, and/or reactive properties described above with respect to the physical or chemical treatments. For example, the surface of the structural support member 20 may include a polymer coating that includes reactive moieties configured to react with functional groups of inner liner 18, outer jacket 24, and/or support layer 22. As a result, the surface of at least the portion of structural support member 20 may include a coating covalently bonded to at least one of inner liner 18 or outer jacket 24.

In some instances, structural support member 20 may be surface treated for contact with only one of inner liner 18 or outer jacket 24. As one example, structural support member 20 may be selectively surface treated on an inner radial surface of structural support member 20 without being surface treated on an outer radial surface of structural support member 20, such that structural support member 20 may have increased adhesion to inner liner 18 or support layer 22 between inner liner 18 and structural support member 20. During positioning of structural support member 20 on inner liner 18, the increased adhesion may reduce movement of structural support member 20. As another example, structural support member 20 may be surface treated on an outer radial surface of structural support member 20 without being surface treated on an inner radial surface of structural support member 20, such that structural support member 20 may have increased adhesion to outer jacket 24 or support layer 22 between outer jacket 24 and structural support member 20. During formation of outer jacket 24, the surface treatment may increase a surface area and/or reactivity of the surface of structural support member 20, such that a material of outer jacket 24 may more strongly bond with the surface of structural support member 20. In other instances, structural support member 20 may be surface treated for contact with both inner liner 18 and outer jacket 24

In some examples, the surface treatment can be applied to, or present in various amounts at, one or more particular portions of structural support member 20 to increase the adhesion between structural support member 20 and inner liner 18 and/or outer jacket 24. For example, these one or more portions that are surface treated can be certain portions of structural support member 20 that may be more likely to experience stresses that can cause separation from inner liner 18 and/or outer jacket 24 than other portions of structural support member 20. For example, a surface of a first portion of structural support member 20, such as a more distal portion, may be surface treated and a surface of a second portion of structural support member 20, such as a more proximal portion, may not surface treated. As a result, the surface of the first portion of structural support member 20 may have different surface properties than the surface of the second portion of structural support member 20. For example, the surface of the first portion of structural support member 20 may have a first surface roughness and a surface of the second portion of structural support member 20 may have a second surface roughness that is less than the first surface roughness. In some examples, a shear strength of the first portion is greater than at least about 20% higher than a shear strength of the second portion.

In some examples, one or more portions of structural support member 20 that may be subject to relatively high deformation may be surface treated. For example, a first portion of structural support member 20 near distal opening 13 may be adjacent to a relatively low durometer section of outer jacket 24 that is more compressible. During navigation of catheter 10 through vasculature, the first portion may experience a relatively high amount of deformation that may cause delamination or detachment of outer jacket 24 from structural support member 20.

In some examples, surfaces of one or more portions of structural support member 20 having a relatively high density (e.g., coil pitch or pics per inch) may be surface treated. For example, a first portion of structural support member 20 may have a relatively high coil pitch and a second portion of structural support member 20 may have a relatively low coil pitch. Due to the higher density, inner liner 18 and outer jacket 24 may have lower inter-coil or inter-braid contact in the first portion than the second portion of structural support member 20. For example, during formation of outer jacket 24, the first portion of structural support member 20 may have reduced flow of an outer jacket material between structures (e.g., adjacent turns of a coil) of structural support member 20. This reduced flow of the outer jacket material may result in reduced contact area between inner liner 18 and outer jacket 24 in the first section compared to the second section, whether directly (as in a tri-layer catheter configuration) or via support layer 22 (as in a quad-layer catheter configuration illustrated in FIG. 2).

In some examples, surfaces of one or more portions of structural support member 20 having a relatively larger diameter may be surface treated. For example, a first portion of structural support member 20 may have a relatively small diameter and a second portion of structural support member 20 may have a relatively large diameter. Due to the larger diameter in the second portion of structural support member 20, inner liner 18 and outer jacket 24 may have lower inter-coil or inter-braid contact area in the second portion than the first portion of structural support member 20.

In the example illustrated in FIG. 2, structural support member 20 is formed from a wire, such as a rounded (in cross-section) wire, that is shaped to define a coil. In other examples, member 20 may be formed, at least in part, from a flat (in cross-section) wire that is shaped to define a coil. A rounded wire may define a coil member having a lower surface area than a flat wire, such that, for a given length of structural support member 20, inner liner 18 and/or outer jacket 24 may have a higher contact area between coils of structural support member 20. A flat wire may define a coil member having a higher surface area than a round wire, such that, for a given length of structural support member 20, structural support member 20 may have a higher contact area with inner liner 18 and/or outer jacket 24.

The wire from which member 20 is formed can be a metal wire. In some examples, the wire is formed from a shape memory material, such a nickel titanium alloy (Nitinol). In other examples, the wire is formed from stainless steel. In some cases, a nickel titanium alloy may be more crush resistant than stainless steel, and, therefore, may be used to form a structural support member 20 of a catheter that is more resistant to kinking and buckling compared to stainless steel. In addition, as described in further detail below, a shape memory material may allow structural support member 20 to be formed before it is positioned over inner liner 18. For example, the pitch and diameter of member 20 may be defined before member 20 is positioned over inner liner 18, which may provide certain advantages (discussed below). In contrast, when member 20 is formed from stainless steel, the pitch and diameter of member 20 may be defined as member 20 is wound over inner liner 18.

In some examples, structural support member 20 includes multiple, longitudinally adjacent structures (e.g., connected to each other, abutting but not connected to each other, or with a gap therebetween). In other examples, structural support member 20 is formed from a single wire that defines a coil member that changes in outer diameter and inner diameter of structural support member 20, changes in outer diameter of the coil member, and changes in pitch along the length of member 20. The single wire may be seamless (or joint-less) in that there are no joints (e.g., butt joints) between separate portions of wire that are connected together to define a longer wire; rather, the wire has a unitary body construction. In some examples, a contemporaneous change in pitch and inner and outer diameters of the structural support member 20 including a single, seamless wire may be made possible, at least in part, by a shape memory material from which the wire is formed. Defining member 20 from a single, seamless wire may increase the structural integrity of catheter body 12 compared to examples in which member 20 is formed from multiple wires that are joined together. For example, the joints between wires may adversely affect the tensile strength or lateral flexibility of member 20, which may adversely affect the flexibility and pushability of catheter body 12.

In examples in which structural support member 20 includes a coil (e.g., a helical coil), the flexibility of structural support member 20 may be, at least in part, a function of a pitch of the coil. For a given wire, a larger pitch results in larger gaps between adjacent turns of the wire forming member 20 and a higher degree of flexibility. The pitch can be, for example, the width of one complete turn of wire, measured in a direction along longitudinal axis 16. In some examples, a pitch of structural support member 20 varies along a length of structural support member 20, such that a stiffness (or flexibility) varies along the length. The pitch may continuously vary along the length of member 20, or may progressively change, e.g., include different sections, each section having a respective pitch.

The flexibility of outer jacket 24 may be, at least in part, a function of a composition, a hardness (e.g., durometer), and/or a thickness of outer jacket 24. For example, a higher durometer may result in less compressibility and a lower degree of flexibility. To configure catheter body 12 with a particular flexibility profile (e.g., a flexibility along longitudinal axis 16), outer jacket 24 may include multiple outer jacket segments that include varied properties and are supported by a variable density structural support member 20. FIGS. 3-4 illustrate various catheters that include variable density structural support members 20 for supporting one or more junctions between segments of outer jacket 24.

FIG. 3 is a conceptual cross-sectional view of a portion 30 of an example catheter body (e.g., catheter body 12 of FIG. 2) including a coiled structural support member 20, where the cross-section is taken through a center of the catheter body and along the longitudinal axis (e.g., longitudinal axis 16 in FIG. 1) of the catheter body. While catheter body 12 is primarily referred to in the description of FIGS. 3 and 4, in other examples, portion 30 can be a portion of another catheter body.

In the example shown in FIG. 3, portion 30 of catheter body 12 includes inner liner 18, outer jacket 24, and structural support member 20. Outer jacket 24 includes a plurality of outer jacket segments 34A and 34B (collectively referred to herein as "segments 34" or generally referred to individually as "segment 34"). In the example of FIG. 3, only a first outer jacket segment 34A and a second outer jacket segment 34B are illustrated; however, catheter body 12 can include any number of outer jacket segments 34. Segments 34 can each be, for example, sleeves (e.g., tubular sleeves) that are configured to be positioned over inner liner 18 and structural support member 20, and, if present, support layer 22, as will be described further in FIGS. 5A-5C.

Segments 34 are situated longitudinally adjacent to each other, e.g., in an abutting relationship, and, in some examples, can be mechanically connected together to define outer jacket 24 using any suitable technique, such as by welding, an adhesive, heating/reflow, or any combination thereof. Adjacent outer jacket segments 34 form a junction 32 between the adjacent outer jacket segments 34; as illustrated in FIG. 3, outer jacket segment 34A forms junction 32 with outer jacket segment 34B. Segments 34 may each have any suitable length, which may be selected based on the desired flexibility profile of catheter body 12. In some examples, proximal, distal, and intermediate portions 17A-17C (FIG. 1) of catheter body 12 may have their own respective outer jacket segments 34 that each begin and end at the proximal and distal ends of the corresponding catheter body portions 17A-17C. In other examples, one of outer jacket segments 34 may extend at least over both proximal portion 17A and intermediate portion 17C, and/or over both intermediate portion 17C and distal portion 17B.

The stiffness and/or hardness (e.g., durometer) of outer jacket 24 contribute to the flexibility and structural integrity of catheter body 12. Accordingly, the composition and properties of each of segments 34, such as durometer and/or thickness, may be selected to assist in providing portion 30 of catheter body 12 with the desired flexibility characteristics.

In some examples, the composition of each of segments 34 may be selected to provide catheter body 12 with the desired flexibility characteristics. For example, different materials may have different properties, such as durometer, compressibility, elasticity, and the like. In some examples, at least two outer jacket segments 34 are formed from different materials (e.g., materials having different chemical compositions and/or different material characteristics). Example materials for segments 34 include, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer or other thermoplastic material, or combinations thereof. In one example, a more proximal segment, such as segment 34A, is formed from an aliphatic polyamide and a more distal segment, such as segment 34B, is formed from a polyether block amide. The compositions of the polyether block amide may be modified to achieve segments 34 having different durometers.

In some examples, the durometers of each of segments 34 may be selected to help provide catheter body 12 with the desired flexibility characteristics. For example, at least two outer jacket segments 34 may have different durometers. In some examples, segments 34 may have a durometer between about 30 A-100 A or 25 D and about 90 D. In other examples, however, one or more of the segments 34 may have other hardness values. The hardness of the segments 34 may be selected to obtain more or less flexibility, torqueability, and pushability for all or part of catheter body 12.

In some examples, such as example portions of catheter body 12 in which catheter body 12 increases in flexibility from proximal end 12A towards distal end 12B, the durometer of two adjacent outer jacket segments 34 may decrease in a direction from a proximal end of outer jacket 24 towards a distal end. For example, a durometer of first outer jacket segment 34A may be greater than a durometer of second outer jacket segment 34B. As a result, catheter body 12 may be more flexible for navigating catheter 10 through vasculature of a patient.

In some examples, such as example portions of catheter body 12 in which catheter body 12 decreases in flexibility along any part of catheter body 12 between from proximal end 12A towards distal end 12B, the durometer of two adjacent outer jacket segments 34 may increase in a direction from a proximal end of outer jacket 24 towards a distal end. For example, a durometer of first outer jacket segment 34A may be less than a durometer of second outer jacket segment 34B. While it may be desirable in some cases to provide a catheter body 12 having a relatively flexible distal portion, as explained above, increasing the durometer of a distal-most section of outer jacket 24 relative to a more proximal section that is directly adjacent to the distal-most section, may provide certain advantages. For example, increasing the durometer of the distal-most section may configure distal opening 13 of catheter body 12 to resist geometric deformation when distal opening 13 (FIG. 1) of catheter body 12 is engaged with a guidewire, which may help support the navigation of catheter body 12 through vasculature. The distal-most section of outer jacket 24 that exhibits the increased stiffness may be a relatively small length of catheter body 12 and, therefore, may not affect the overall flexibility of catheter body 12.

In some examples, structural support member 20 includes one or more sections that includes different properties related to a flexibility of catheter body 12, such as density of structures of structural support member 20 and diameter of structural support member 20. In the example of FIG. 3, structural support member 20 includes a first section 36A, a second section 36B distal to first section 36A, and a third section 36C distal to second section 36B (referred to collectively as "sections 36" and individually generically as "section 36").

In some examples, structural support member 20 includes one or more relatively high density sections 36 interspersed with relatively low density sections 36. Due to discontinuities between and/or different properties of the adjacent outer jacket segments 34, junction 32 between adjacent outer jacket segments 34 may be a relatively weak spot at which catheter body 12 may be more likely to buckle, kink, or collapse. As explained above, a density of structural support member 20 may be inversely proportional to a compressibility of structural support member 20, such that the relatively high density sections of structural support member 20 may lower flexibility and/or higher compressibility than the relatively low density sections of structural support member 20. In some examples, to reinforce junction 32, structural support member 20 has a variable density that is higher near junction 32. For example, in the example of FIG. 3, first section 36A of structural support member 20 has a first density, second section 36B of structural support member 20 has a second density, and third section 36C of structural support member 20 has a third density, where the second density of second section 36B is higher than the first and third densities of first section 36A and third section 36C, respectively.

In some examples, structural support member 20 includes a coil comprising different sections having different, respective pitches. An increasing density of structural support member 20 may correspond to a decreasing pitch (e.g., spacing between coils or braids) of structural support member 20. As shown in FIG. 3, a pitch of structural support member 20 decreases in a distal direction from first section 36A to second section 36B and increases in the distal direction from second section 36B to third section 36C. In one example, a pitch of a higher density section of structural support member 20, such as second section 36B, may be greater than about 25% and less than about 75% of a pitch of an adjacent lower density portion 36 of structural support member 20, such as first section 36A or third section 36C. While sections 36 are illustrated as having transition in density that are step-wise, in some examples, transitions in density of structural support member 20 may be gradual. In some examples, a pitch of structural support member may be between about 0.00225 inches (about 0.057 mm) to about 0.0070 inches (about 0.018 mm).

Second section 36B is longitudinally aligned with junction 32 between first outer jacket segment 34A and second outer jacket segment 34B. For example, second section 36B may longitudinally overlap a portion of first outer jacket segment 34A and second outer jacket segment 34B, such as greater than about 5 mm (measured along longitudinal axis 16). The relatively high density of second section 36B may enable portion 30 of catheter body 12 to resist compression, and therefore buckling, at junction 32, such that structural support member 20 may be less likely to collapse at junction 32 in response to compression or bending forces experienced while navigating catheter 10 through the vasculature of a patient compared to catheters that do not include a relatively high density section of a structural support member at a junction between two adjacent outer jacket segments.

In some examples, a surface of one or more sections of structural support member 20 may be surface treated to increase an adhesion of the surface to at least one of inner liner 18 and/or outer jacket 24. For example, as explained with respect to FIG. 2 above, a portion of structural support member 20 having a relatively high density may exhibit a reduced flow of outer jacket material between structures of structural support member 20 and/or reduced contact area with inner liner 18 and/or support layer 22. The surface treatment may help compensate for any adverse impacts to the kink, compression, or buckling of catheter body 12 resistance attributable to this reduced contact area. In the example of FIG. 3, second section 36B includes a higher density, such that at least second section 36B of structural support member 20 may be surface treated to increase an adhesion of the surface of second section 36B to at least one of inner liner 18 and/or first outer jacket segment 34A and/or second outer jacket segment 34B.

During navigation of catheter 10 through vasculature of a patient, bending of catheter body 12 may exert compressive forces on an inside radius of catheter body 12, such as at portion 30. Without variable density structural support member 20, the compressive forces may cause portion 30 to kink or buckle near junction 32. However, the higher density of second section 36B of structural support member 20 may reinforce junction 32 to more evenly distribute forces, such as to portions of catheter body 12 that are adjacent to junction 32.

In some instances, a variable density structural support member, in combination with a variable composition, durometer, and/or thickness outer jacket 24, may further configure a flexibility of a catheter body. FIG. 4 is a conceptual cross-sectional view of a portion 40 of a catheter body (e.g., catheter body 12 of FIG. 2) including a braided structural support member 21, where the cross-section is taken through a center of catheter body 12 and along a longitudinal axis of catheter body 12. Braided structural support member 21 may be an example of structural support member 20 of FIG. 2, such that features of braided structural support member 21 may apply to structural support member 20 of FIG. 2, and vice versa.

Portion 40 of catheter body 12 includes inner liner 18, outer jacket 24, and structural support member 21. Outer jacket 24 includes a plurality of outer jacket segments 44A, 44B, and 44C (collectively referred to herein as "segments 44" or generally referred to individually as "segment 44"). In the example of FIG. 4, only a first outer jacket segment 44A, a second outer jacket segment 44B, and a third outer jacket segment 44C are illustrated; however, portion 40 and catheter body 12 can include any suitable number of outer jacket segments 44 in other examples. Adjacent outer jacket segments 44 form a junction 42 between the adjacent outer jacket segments 44; as illustrated in FIG. 4, outer jacket segment 44A forms junction 42A with outer jacket segment 44B and outer jacket segment 44B forms junction 42B with outer jacket segment 44C. Segments 44 may be similar to segments 34 of FIG. 3 described above.

In some examples, structural support member 21 includes one or more sections that include different properties related to a flexibility of catheter body 12, such as density of structures of structural support member 21 and diameter of structural support member 21. In the example of FIG. 4, structural support member 21 includes a first section 46A, a second section 46B distal to first section 46A, and a third section 46C distal to second section 46B (referred to collectively as "sections 46" and individually generically as "section 46"). Sections 46 may be similar to sections 36 of FIG. 3 described above.

In some examples, structural support member 21 may be configured to reinforce one or more junctions 42 and one or more outer jacket segments 44. For example, the flexibility of catheter body 12 may be, at least in part, a function of the flexibility of structural support member 21 and outer jacket 24. As such, the various flexibility properties of different structural support member sections 46 and outer jacket segments 44 may be configured to, in combination, produce a desired flexibility profile of portion 40 of catheter body 12.

As one example, in the example of FIG. 4, first section 46A of structural support member 21 is adjacent (e.g., in a radial direction) to first outer jacket segment 44A, second section 46B of structural support member 21 is adjacent to second outer jacket segment 44B, and third section 46C of structural support member 21 is adjacent to third outer jacket segment 44C. Outer jacket 24 may exhibit a gradually decreasing durometer, such that first outer jacket segment 44A has a first durometer, second outer jacket segment 44B has a second durometer that is lower than the first durometer of first outer jacket segment 44A, and third outer jacket segment 44C has a third durometer that is lower than the first and second durometers of first outer jacket segment 44A and second outer jacket segment 44B, respectively. First section 46A of structural support member 21 has a first density, second section 46B of structural support member 21 has a second density, and third section 46C of structural support member 21 has a third density, such that the second density of second section 46B is higher than the first and third densities of first section 46A and third section 46C, respectively. As a result, portion 40 forms a generally three-part catheter body 12 that includes a proximal portion having a relatively low density and relatively high durometer for a relatively low net flexibility, an intermediate portion having a relatively high density and relatively moderate durometer for a relatively moderate net flexibility, and a distal portion having a relatively low density and relatively low durometer for a relatively high net flexibility. As shown in FIG. 4, second section 46B overlaps a portion of each of first outer jacket segment 44A and third outer jacket segment 44C to reinforce junctions 42A and 42B. In this way, catheter bodies incorporating variable flexibility features in structural support member 21 and outer jacket 24 may configure more specific flexibility profiles with increased structural integrity.

Figure 5A:
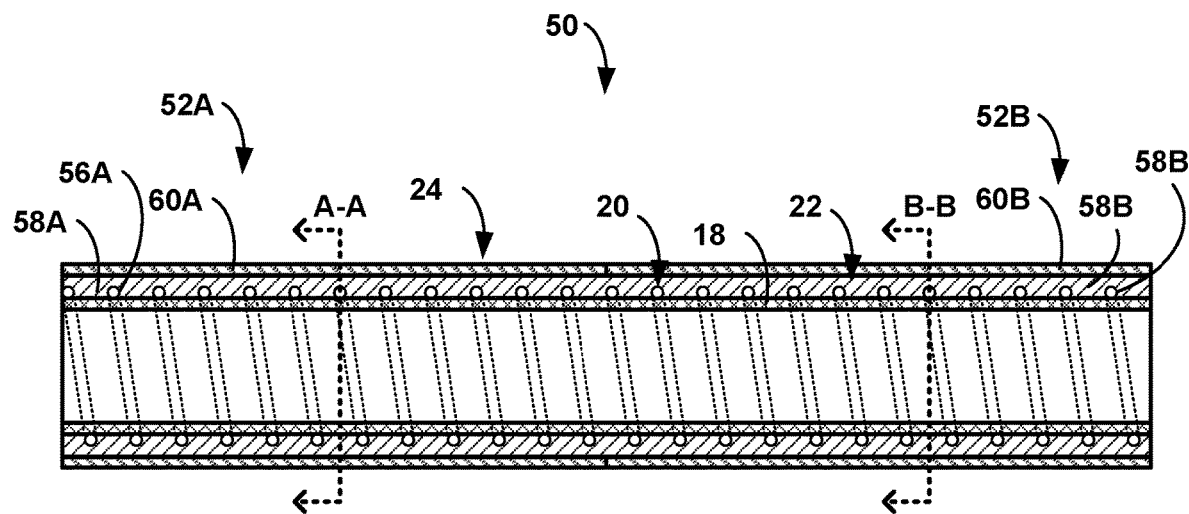
FIG. 5A is a conceptual cross-sectional view of a part of a catheter body including a tapered structural support member, where the cross-section is taken through a center of the catheter body and along a longitudinal axis of the catheter body.

In some examples, catheters described herein may include a structural support member that may change in diameter along a length of the structural support member. FIG. 5A is a conceptual cross-sectional view of a part of a catheter body including a tapered structural support member, where the cross-section is taken through a center of the catheter body and along a longitudinal axis of the catheter body. Portion 50 of catheter body 12 includes inner liner 18, outer jacket 24, structural support member 20, and support layer 22. However, in other examples, such as catheter bodies or portions of catheter bodies that include a tri-layer configuration, support layer 22 may not be included. Portion 50 includes a proximal portion 52A and a distal portion 52B.

Figure 5B:
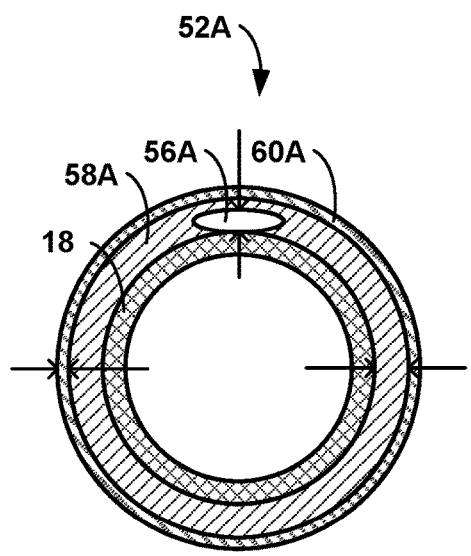
FIG. 5B is a conceptual cross-sectional view of the catheter body of FIG. 5A taken along line A-A in FIG. 5A.
Figure 5C:
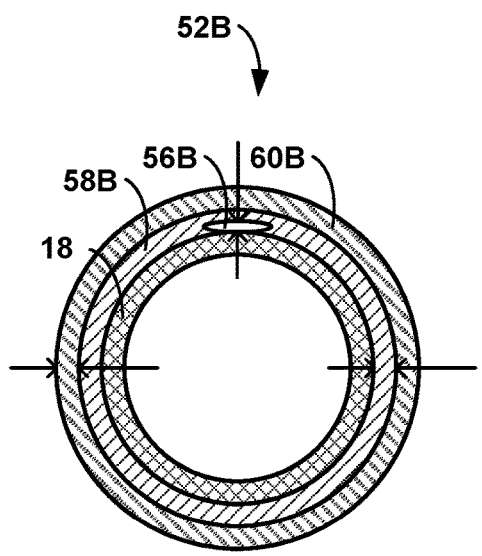
FIG. 5C is a conceptual cross-sectional view of the catheter body of FIG. 5A taken along line B-B in FIG. 5A.

FIG. 5B is a conceptual cross-sectional view of proximal portion 52A of portion 50 of catheter body 12 of FIG. 5A taken along line A-A in FIG. 5A, while FIG. 5C is a conceptual cross-sectional view of distal portion 52B of portion 50 of catheter body 12 of FIG. 5A taken along line B-B in FIG. 5A. In the examples of FIG. 5A-5C, outer jacket 24 includes a proximal outer jacket segment 60A and a distal outer jacket segment 60B (collectively referred to as "segments 60" and individually referred to as "segment 60"); support layer 22 includes a proximal section 58A and a distal section 58B (collectively referred to as "segments 58" and individually referred to as "segment 58"); and structural support member 20 includes a proximal section 56A and a distal section 56B (collectively referred to as "section 56" and individually referred to as "section 56").

In some examples, structural support member 20 may taper and/or expand at various portions, such as portion 50, of catheter body 12. As illustrated in the example portion 50 of FIGS. 5A-5C, structural support member 20 tapers from a first diameter at proximal portion 52A to a second diameter at distal portion 52B. For example, structural support member 20 may taper from a first, larger coil diameter to a second, smaller coil diameter. The diameter can be measured, for example, an inner diameter of structural support member 20 and/or an outer diameter of structural support member 20. In the example shown in FIGS. 5A-5C, proximal section 56A of structural support member 20 has a first coil outer diameter and distal section 56B of structural support member 20 has a second coil outer diameter that is smaller than the first coil outer diameter, such that structural support member 20 tapers from the first coil outer diameter to the second coil outer diameter.

In other examples in which inner liner 18 also tapers from a first outer (and/or inner) diameter to a second outer (and/or inner) diameter (smaller than the first outer (and/or inner) diameter), examples in which catheter body 12 tapers from a first outer diameter to a second outer diameter, or both, structural support member 20 may taper to follow the change in the outer diameter of inner liner 18, catheter body 12, or both inner liner 18 and catheter body 12.

In some examples, at least two outer jacket segments 60 have different thicknesses or diameters. For example, a lower diameter portion of structural support member 20, such as a smaller diameter distal section, may have increased flexibility and may enable a thicker outer jacket having a lower durometer, and therefore more flexible, material, while also enabling the catheter to maintain a relatively constant inner diameter of inner liner 18 and outer diameter of outer jacket 24.

In some examples, such as examples in which structural support member 20 decreases in outer diameter (e.g., tapers) from proximal end 12A towards distal end 12B as illustrated in FIG. 1, the thickness of each of outer jacket segments 60 may increase in a direction from a proximal end of outer jacket 24 towards a distal end. For example, outer jacket 24 may expand from a first inner diameter to a second, larger inner diameter. In the example shown in FIGS. 5B and 5C, proximal outer jacket segment 60A has a first jacket inner diameter and distal outer jacket segment 60B has a second jacket inner diameter, such that outer jacket 24 expands from the first jacket inner diameter to the second jacket inner diameter. As a result, a thickness of proximal outer jacket segment 60A may be less than a thickness of distal outer jacket segment 60B and a thickness of proximal section 58A of support layer 22 may be greater than a thickness of distal section 58B of support layer 22.

In some examples, such as examples in which catheter body 12 tapers in outer diameter proximate to distal end 12B as shown in FIG. 1, the thickness of adjacent outer jacket segments 60 may decrease in a direction from the proximal end of outer jacket 24 towards the distal end. For example, a thickness of first outer jacket segment 60A may be greater than a thickness of second outer jacket segment 60B. In some examples, at least two segments 60 may also define different inner diameters than each other, where the inner diameter of a particular segment 60 may be selected to accommodate the portion of catheter body 12 in which a sleeve corresponding to the segment 60 is to be positioned. In some examples, each segment 60 has the same wall thickness (measured in a direction orthogonal to longitudinal axis 16 (FIG. 1). In other examples, the wall thicknesses of segments 60 may differ.

Figure 6:
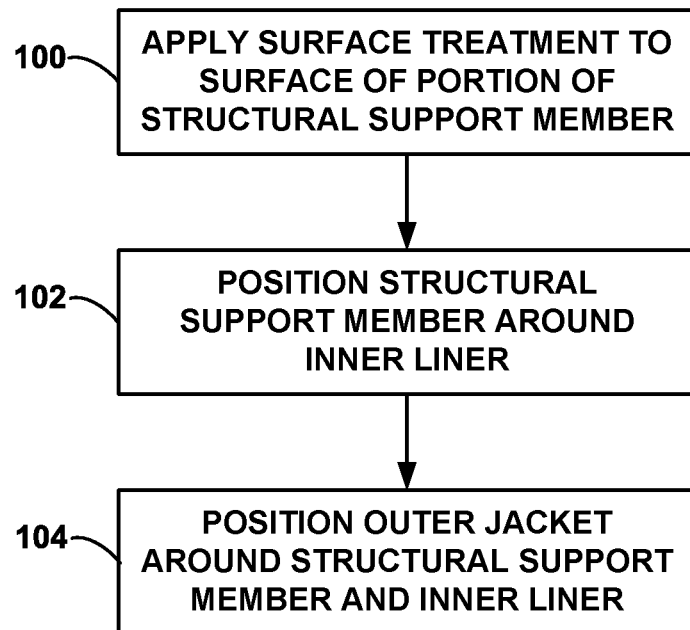
FIG. 6 is a flow diagram of an example method of forming the catheters of FIGS. 1-5.
Figure 7:
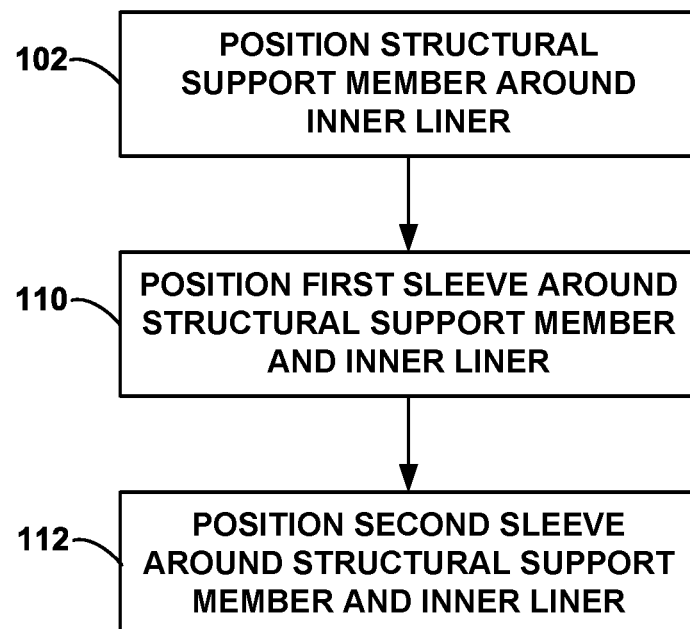
FIG. 7 is a flow diagram of an example method of forming the catheters of FIGS. 1-5.

The catheters described herein can be formed using any suitable technique. FIGS. 6 and 7 are flow diagrams of example methods of forming any of catheter 10 of FIGS. 1 and 2, portion 30 of FIG. 3, portion 40 of FIG. 4, and/or portion 50 of FIGS. 5A-5C. FIG. 6 is a flow diagram of an example method of forming the catheters of FIGS. 1-5 having a surface-treated structural support member, and will be described with reference to catheter 10 of FIG. 1.

In accordance with the technique shown in FIG. 6, structural support member 20 is surface treated by at least applying a surface treatment to a surface of at least a portion of structural support member 20 to increase adhesion of structural support member 20 to inner liner 18 and/or outer jacket 24. In some examples, the surface treatment is applied to the entire structural support member 20. In other examples, the surface treatment is applied to only a portion, such that other portions of structural support member 20 remain untreated in the same manner. As an example, in some instances, structural support member 20 may be surface treated for contact with only one of inner liner 18 or outer jacket 24. In some examples, applying the surface treatment includes applying the surface treatment to an inner radial surface of structural support member 20 without substantially applying the surface treatment to an outer radial surface of structural support member 20, such that structural support member 20 may have increased adhesion to inner liner 18 or support layer 22 between inner liner 18 and structural support member 20. For example, a surface treatment may be directed to the inner radial surface of structural support member 20; while there may be unintentional treatment of some surfaces of the outer radial surface of structural support member 20 during this process, a majority of the outer radial surface may remain untreated by the surface treatment.

In some examples, applying the surface treatment includes applying the surface treatment to an outer radial surface of structural support member 20 without substantially applying the surface treatment to an inner radial surface of structural support member 20, such that structural support member 20 may have increased adhesion to outer jacket 24 or support layer 22 between outer jacket 24 and structural support member 20.

In some examples, the surface treatment includes a physical treatment, alone or in combination with the other surface treatments described herein. A physical treatment includes any treatment that may result in an increase in contact area of the surface of structural support member 20 for bonding with inner layer 18, outer jacket 24, and/or support layer 22, or an increase in mechanical interlocking between the surface of structural support member 20 and inner liner 18, outer jacket 24, and/or support layer 22. For example, a physical treatment may increase a surface area or surface deviation (e.g., slope angle) of the surface of structural support member 20. A variety of physical treatments may be used including, but not limited to, mechanical roughening, laser roughening, abrasion, and the like.

In some examples, applying the surface treatment includes roughening the surface of at least the portion of the structural support member to increase a surface roughness of the surface. An increased surface roughness may be, for example, an increased contact area, contact slope, and/or fractality of the surface of structural support member 20 with inner liner 18, outer jacket 24, and/or support layer 22, thereby increasing adhesion between structural support member 20 and inner liner 18, outer jacket 24, and/or support layer 22. In some examples, the surface of at least the portion of the structural support member includes a surface roughness greater than about [minimum surface roughness measurement].

In some examples, the surface treatment includes a chemical treatment, alone or in combination with the other surface treatments described herein. A chemical treatment includes any treatment that may result in an increase in chemical bonding between structural support member 20 and inner liner 18, outer jacket 24, and/or support layer 22. For example, a chemical treatment may increase a charge or reactivity of the surface of structural support member 20 to increase intermolecular forces between structural support member 20 and inner liner 18, outer jacket 24, and/or support layer 22. A variety of chemical treatments may be used including, but not limited to, alkaline treatment, acid treatment, ionization, protonation, deprotonation, electric field charge, and the like.

In some examples, applying the surface treatment includes chemically treating the surface of at least the portion of structural support member 20 to increase a charge of the surface. An increased charge of the surface may be opposite to a charge of the inner liner, the outer coating, and/or the support layer, thereby increasing an electrostatic attraction between the structural support member and the inner liner, outer jacket, and/or support layer. For example, structural support member 20 may include a positive charge, while outer jacket 24 may include a negative charge, such that structural support member 20 and outer jacket 24 may be electrostatically attracted to each other.

In some examples, applying the surface treatment includes chemically treating the surface of at least the portion of structural support member 20 to functionalize the surface with reactive moieties. For example, the surface of structural support member 20 may be reacted with an acid or base to create reactive moieties, such as amines, carboxylic acids, or other reactive groups configured to react with polymers. Inner liner 18, outer jacket 24, and/or support layer 22 may include polymers that include various functional groups capable of reacting with the reactive moieties on structural support member 20. Reactive moieties on the structural support layer may bond (e.g., covalently) with the functional groups of inner liner 18, outer jacket 24, and/or support layer 22. As a result, the surface of at least the portion of structural support member 20 may be covalently bonded to at least one of inner liner 18 or outer jacket 24.

In some examples, the surface treatment may include a coating treatment, alone or in combination with the other surface treatments described herein. The coating treatment can include, for example, coating the surface of a portion of the structural support member with a functional layer, such as a reactive layer with reactive moieties. Rather than provide surface properties through a direct surface treatment of the structural support member, a functional layer may provide the roughness, charge, and/or reactive properties described above with respect to the physical or chemical treatments. In some examples, applying the surface treatment includes coating the surface of at least the portion of structural support member 20 with a reactive layer with reactive moieties. For example, the surface of the structural support member 20 may include a polymer coating that includes reactive moieties configured to react with functional groups of inner liner 18, outer jacket 24, and/or support layer 22, such that the coating may be covalently bonded to at least one of inner liner 18 or outer jacket 24.

In some examples, applying the surface treatment includes applying the surface treatment to, or in various amounts at, particular portions of structural support member 20 to increase the adhesion between structural support member 20 and inner liner 18 and/or outer jacket 24. For example, a surface of a first portion of structural support member 20, such as a more distal portion, may be surface treated and a surface of a second portion of structural support member 20, such as a more proximal portion, may not be surface treated or can be treated in a different way. As a result, the surface of the first portion of structural support member 20 may have different surface properties than the surface of the second portion of structural support member 20. In some examples, the surface of the first portion of structural support member 20 may have a first surface roughness and a surface of the second portion of structural support member 20 may have a second surface roughness that is less than the first surface roughness. In some examples, a shear strength of the first portion is greater than at least 20% higher than a shear strength of the second portion.

In some examples, the surface treatment may be applied to one or more portions of structural support member 20 that may be subject to relatively high deformation. For example, a first portion of structural support member 20 near distal opening 13 may be adjacent to a relatively low durometer section of outer jacket 24 that is more compressible. During navigation of catheter 10 through vasculature, the first portion may experience a relatively high amount of deformation that may cause delamination or detachment of outer jacket 24 from structural support member 20. Thus, the first portion may include the surface treatment to help compensate for the stresses that may cause delamination or detachment of outer jacket 24 from structural support member 20.

In some examples, the surface treatment may be applied to one or more portions of structural support member 20 having a relatively high density. For example, a first portion of structural support member 20 may have a relatively high coil pitch or pics per inch and a second portion of structural support member 20 may have a relatively low coil pitch or pics per inch. Due to the higher coil pitch, inner liner 18 and outer jacket 24 may have lower inter-coil or inter-braid contact in the first portion than the second portion of structural support member 20. For example, during positioning of outer jacket 24 described below, the first portion of structural support member 20 may have reduced flow or reflow of an outer jacket material between structures (e.g., coils) of structural support member 20. This reduced flow of the outer jacket material may result in reduced contact area between inner liner 18 and outer jacket 24 in the first section compared to the second section, whether directly (as in a tri-layer catheter configuration) or via support layer 22 (as in a quad-layer catheter configuration illustrated in FIG. 2).

For example, in the example of FIG. 2, structural support member 20 is a coiled structural support member, and may include a first portion having a first coil pitch and a second portion having a second coil pitch that is less than the first coil pitch. In some examples, applying the surface treatment includes applying the surface treatment to a surface of the first portion of structural support member 20 and refraining from applying a surface treatment to a surface of the second portion of structural support member 20. For example, applying the surface treatment may include roughening a surface of the first portion of structural support member 20 without roughening a surface of the second portion of structural support member 20. In some examples, applying the surface treatment includes applying the surface treatment to a surface of the first portion of structural support member 20 and applying the surface treatment to a surface of the second portion of structural support member 20 to a lesser degree than the first portion of structural support member 20. For example, applying the surface treatment may include roughening a surface of the first portion of structural support member 20 to a first surface roughness and roughening a surface of the second portion of structural support member 20 to a second surface roughness that is less than the first surface roughness. As another example, applying the surface treatment may include chemically treating a surface of the first portion of the coiled structural support member to a first charge and chemically treating a surface of the second portion of the coiled structural support member to a second charge that is less than the first charge.

In some examples, the surface treatment may be applied to one or more portions of structural support member 20 having a relatively large inner or outer diameter. For example, a first portion of structural support member 20 may have a relatively small diameter and a second portion of structural support member 20 may have a relatively large diameter. Due to the greater diameter in the second portion of structural support member 20, inner liner 18 and outer jacket 24 may have lower inter-coil or inter-braid contact area in the second portion than the first portion of structural support member 20.

At any time prior to positioning structural support member 20 over inner liner 18 (102), inner liner 18 may be positioned over a mandrel (not shown). In some examples, inner liner 18 may be positioned over the mandrel by at least inserting the mandrel through an end of inner liner 18. After positioning inner liner 18 over the mandrel, surface-treated structural support member 20 may be positioned over inner liner 18 (102). In examples in which structural support member 20 includes a coil member, the wire defining the coil member may be wound over an outer surface of inner liner 18 or pushed over inner liner 18. The coil member can be, for example, a single coil member that is devoid of any joints. In some examples, the structural configuration of structural support member 20 may be at least partially defined as it is wound over inner liner 18 in some examples. For examples, a shape memory wire or a stainless steel wire may be wound over inner liner 18 to define the desired coil pitch, the desired diameter(s), the desired taper, the desired length, or any combination thereof of member 20. The shape memory wire may then be heat set to define structural support member 20.

Structural support member 20 may be secured in place relative to inner liner 18 using any suitable technique. In some examples, outer jacket 24 may at least partially secure structural support member 20 to inner liner 18. After structural support member 20 is positioned over inner liner 18 (102), outer jacket 24 is positioned over an outer surface of structural support member (104). During and/or after positioning outer jacket 24, material of outer jacket 24 may be flowed and/or reflowed between structures (e.g., coils or braids) of structural support member 20, such that at least a portion of a volume between the structures of structural support member 20 may be filled with the material of outer jacket 24. In some instances, the material of outer jacket 24 may contact inner liner 18 to form an interface between inner liner 18 and outer jacket 24. This interface may provide adhesion between inner liner 18 and outer jacket 24, in addition to adhesion between structural support member 20 and inner liner 18 or outer jacket 24. Regardless of whether inner liner 18 and outer jacket 24 form an interface, outer jacket 24 may provide longitudinal support for structural support member 20, such that outer jacket 24 may at least partially limit movement of structural support member 20 between inner liner 18 and outer jacket 24. In this way, outer jacket 24 may assist in integrating structural support member 20 into catheter body 12.

In some examples, an adhesive and/or a polymer, such as support layer 22, may be used to secure structural support member 20 to inner liner 18. As noted above, in some examples, catheter body 12 includes support layer 22. To form support layer 22, a layer of a thermoplastic or a thermoset polymer may be applied over structural support member 20 after structural support member 20 is positioned over inner liner 18 (102), while in other examples, a layer of a thermoplastic or a thermoset polymer may be applied over inner liner 18 prior to positioning structural support member 20 over inner liner 18. The thermoset polymer may be, for example, a viscoelastic thermoset polyurethane (e.g., Flexobond 430). At least some of the polymer may be positioned between the turns of the wire defining member 20.

Positioning the thermoset polymer over inner liner 18 and structural support member 20 in this manner may help bond inner liner 18 and structural support member 20 to outer jacket 24 through support layer 22. For example, the polymer may contact surfaces of structural support member 20, including surfaces of structural support member 20 having a surface treatment, and provide a surface for bonding to outer jacket 24. In contrast, depositing a polymer over inner liner 18 prior to positioning structural support member 20 may lead to surfaces of structural support member 20 void of the polymer, where such surfaces may not as readily or strongly bond with outer jacket 24 as surfaces of support layer 22. After the polymer is positioned over inner liner 18 and structural support member 20 (not shown), the polymer is cured (not shown), e.g., by heating and/or time-curing. In other examples, the polymer can be cured after outer jacket 24 is positioned over inner liner 18, structural support member 20, and the polymer.

Outer jacket 24 may then be positioned over inner liner 18, structural support member 20, and support layer 22 (104). In some examples, outer jacket 24 is adhered to an outer surface of structural support member 20, e.g., an adhesive and/or a polymer may be applied to outer surface of member 20 prior to positioning outer jacket 24 over member 20 and then cured after outer jacket 24 is positioned over member 20. In addition to, or instead of, the adhesive, outer jacket 24 may be heat shrunk over member 20 and inner liner 18. In some examples, the heat shrinking of outer jacket 24 helps secure member 20 in place relative to inner liner 18.

In some examples, inner liner 18, outer jacket 24, and/or support layer 22 may directly physically interact with the surface-treated structural support member 20. As one example, structural support member 20 may have increased friction and/or bonding surface with inner liner 18, outer jacket 24, and/or support layer 22. An increased surface roughness may increase contact area, contact slope, and/or fractality of the surface of structural support member 20 with inner liner 18, outer jacket 24, and/or support layer 22, thereby increasing adhesion between structural support member 20 and inner liner 18, outer jacket 24, and/or support layer 22. As another example, structural support member 20 may have increased mechanical interlocking with outer jacket 24 and/or support layer 22. For example, a material of outer jacket 24 and/or support layer 22 may flow or permeate into local deviations of the surface of structural support member 20 caused by increased roughness.

In some examples, inner liner 18, outer jacket 24, and/or support layer 22 may chemically interact with the surface-treated structural support member 20. As one example, an increased charge of the surface of structural support member 20 may be opposite to a charge of inner liner 18, outer jacket 24, and/or support layer 22, thereby increasing an electrostatic attraction between structural support member 20 and inner liner 18, outer jacket 24, and/or support layer 22. As another example, inner liner 18, outer jacket 24, and/or support layer 22 may include polymers that include various functional groups capable of reacting with the reactive moieties on structural support member 20. Reactive moieties on structural support member 20 may bond (e.g., covalently) with the functional groups of inner liner 18, outer jacket 24, and/or support layer 22, such that the surface of at least the portion of structural support member 20 may be covalently bonded to at least one of inner liner 18 or outer jacket 24.

FIG. 7 is a flow diagram of an example method of forming the catheters of FIGS. 1-5 including an outer jacket having a plurality of outer jacket segments, and will be described with reference to portion 30 of catheter body 12 of FIG. 3. In accordance with the technique shown in FIG. 7, structural support member 20 may be positioned over inner liner 18 (102), as described above with respect to FIG. 6.

Structural support member 20 includes one or more relatively high density sections interspersed with relatively low density sections. In the example of FIG. 3, first section 36A of structural support member 20 has a first density, second section 36B of structural support member 20 has a second density, and third section 36C of structural support member 20 has a third density, such that the second density of second section 36B is higher than the first and third densities of first section 36A and third section 36C, respectively.

In some examples, the structural configuration of structural support member 20 may be at least partially defined prior to being positioned over inner liner 18. For example, a shape memory wire (e.g., a nickel-titanium wire) or a wire of an otherwise heat-settable metal or alloy may be wound over a different mandrel (e.g., a "coil mandrel") on which inner liner 18 is not present or over the mandrel (e.g., before inner liner 18 is positioned on the mandrel) to define at least one of the desired coil pitch, the desired coil diameter, the desired tapering profile (e.g., a continuous tapering or progressive tapering), or the desired length of structural support member 20, and then heat set to substantially hold its shape. The wire may then be subsequently unwound from the mandrel onto a reel or a bobbin, and then positioned over inner liner 18. Structural support member 20 may be positioned over inner liner 18 by, for example, winding member 20 over inner liner 18 (e.g., winding member 20 from the bobbin or reel onto inner liner 18) or by pushing inner member 20 over an end of inner liner 18.

In some examples, a wire formed from a shape memory metal/alloy or an otherwise heat-settable metal/alloy may be preformed into a helical coil having a constant pitch and the desired diameters, including the desired taper, and then, once positioned over inner liner 18, the layout of the coiled wire may be adjusted to achieve the desired pitch profile (e.g., the change in pitch over the length) of structural support member 20. For example, the pitch of the wire may be adjusted over inner liner 18 to achieve the desired pitch profile. These adjustments may be made manually, by hand, or by a computer-controlled device. In other examples, however, a wire may be preformed into a helical coil having the desired pitch profile and diameters for structural support member 20 before being positioned over inner liner 18.

Defining some or all of the structural characteristics of structural support member 20 prior to positioning member 20 over inner liner 18 may help control the structural characteristics of structural support member 20, as well as control the uniformity of the structural support member 20 of multiple catheter bodies. Pre-shaping and shape-setting the member 20 as a coil (as opposed to ordinary wire stock) causes the member 20 to conform closely to the inner liner 18 as the member 20 is wound onto the liner 18. This close conformance, on its own and in combination with the resulting reduced need for adhesives or other measures to keep the wound member in place on the liner 18, helps reduce the wall thickness T in the catheter body 12. In addition, shape-setting the structural support member 20 on a separate, heat-resistant mandrel enables the construction of the catheter body 12 using the member 20 on a mandrel made of PTFE or other lubricious, non-heat resistant material.

After structural support member 20 is positioned over inner liner 18 (102), outer jacket 24 is positioned over structural support member 20 and inner liner 18 to form catheter body 12. Outer jacket 24 includes a plurality of outer jacket segments 34, such that positioning outer jacket 24 over structural support member 20 and inner liner 18 may include positioning a plurality of sleeves around structural support member 20 and inner liner 18. For example, each sleeve may be slid over the outer surface of member 20 and positioned longitudinally adjacent to at least one other sleeve. Each sleeve of the plurality of sleeves may correspond to one or more outer jacket segments 34.

The sleeves may have different compositions and/or properties. For example, at least two sleeves may have different materials, different durometers, and/or different thicknesses. In some examples, a sequence in which the sleeves may be positioned may define increasing or decreasing flexibility of catheter body 12. As one example, to increase flexibility from a proximal to a distal end of portion 30, a durometer of a first sleeve is greater than a durometer of the second sleeve, such that a durometer of first outer jacket segment 34A is greater than a durometer of second outer jacket segment 34B. As another example, to decrease flexibility from a proximal to a distal end of portion 30, a durometer of first sleeve is less than a durometer of the second sleeve, such that a durometer of first outer jacket segment 34A is less than a durometer of second outer jacket segment 34B.

In the example of FIG. 7, forming outer jacket 24 includes positioning a first sleeve corresponding to first outer jacket segment 34A over structural support member 20 (110) and positioning a second sleeve corresponding to second outer jacket segment 34B over structural support member 20, distal to the first sleeve (112). The first and second sleeves may be positioned such that second section 36B of structural support member 20 is longitudinally aligned with junction 32 between first outer jacket segment 34A and second outer jacket segment 34B. Upon finishing construction of catheter body 12, structural support member 20 will have a variable density that is higher near junction 32, thereby enforcing junction 32.

After positioning outer jacket segments 34, outer jacket segments 34 may be mechanically connected together at junction 32 and configured to substantially conform to the outer surface of structural support member 20, inner liner 18, and/or a support layer (not shown) using any suitable technique. In some examples, segments 34 are formed from a flowable/reflowable material. Heat may be applied to segments 34 to cause at least a portion of segments 34 to melt and flow into spaces between structures of structural support member 20. The heat may cause segments 34 to at least partly fuse together to define a substantially continuous outer jacket 24. The use of heat to apply outer jacket 24 to the subassembly including inner liner 18 and structural support member 20 may help eliminate the need for an adhesive and/or support layer between structural support member 20 and outer jacket 24.

In some examples, segments 34 are formed from a heat shrinkable material. A heat shrink tube may be positioned over segments 34, and heat may be applied to cause the heat shrink tube to wrap tightly around segments 34. The heat and wrapping force may cause segments 34 to fuse together to define a substantially continuous outer jacket 24. The heat shrunk tube may then be removed from the assembly, e.g., via skiving or any suitable technique. The use of heat shrinking to apply outer jacket 24 to the subassembly including inner liner 18, a support layer (optional and not shown), and structural support member 20 may help eliminate the need for an adhesive between structural support member 20 and outer jacket 24. This may help minimize the wall thickness of catheter body 12 and, therefore, increase the inner diameter of catheter body 12 for a given outer diameter. In addition, the absence of an adhesive layer adhering structural support member 20 to outer jacket 24 may contribute to an increased flexibility of catheter body 12.

In some examples, as will be described with reference to FIG. 1 unless otherwise indicated, a method of using catheter 10 includes introducing catheter 10 into vasculature (e.g., an intracranial blood vessel) of a patient via an access point (e.g., a femoral artery or a radial artery), and guiding catheter body 12 through the vasculature. In some instances, catheter body 12 may encounter tortuous vasculature that exerts a bending or compressive force on catheter body 12 in response to a pushing or rotating force at a proximal end of catheter 10. As catheter body 12 is advanced through the tortuous vasculature, catheter body 12 may resist kinking or buckling. As one example, as illustrated in FIG. 2, structural support member 20 may remain adhered to outer jacket 24 and/or inner liner 12, at least partly due to increase adhesion from one or more surface-treated surfaces of structural support member 20. As another example, as illustrated in portion 30 of FIG. 3, structural support member 20 may support a junction 32 between segments 34 of outer jacket 24 to resist buckling near junction 32. As another example, as illustrated in portion 40 of FIG. 4, structural support member 20 may provide for greater variation in flexibility along catheter body 12. As another example, as illustrated in portion 50 of FIG. 5, outer jacket 24 may provide for greater variation in flexibility and/or compressibility while retaining a relatively constant inner and outer diameter of catheter body 12. In these various ways, catheter body 12 may be increase flexibility and/or pushability of catheter 10 through tortuous vasculature of a patient. Any of the examples of catheter body 12 characteristics that contribute to a resistance to kinking or buckling can be used in combination with each other.

Once distal end 12B of catheter body 12 is positioned at the target tissue site, which may be proximal to thromboembolic material (e.g., a thrombus), the thromboembolic material be removed from the vasculature via catheter body.

12. For example, the thromboembolic material may be aspirated from the vasculature by at least applying a vacuum force to inner lumen 26 of catheter body 12 via hub 14 (and/or proximal end 12A), which may cause the thromboembolic material to be introduced into inner lumen 26 via distal opening 13. Optionally, the vacuum or aspiration can be continued to thereby draw the thromboembolic material proximally along the inner lumen 26, all or part of the way to the proximal end 12A or hub 14. As a further option, the aspiration or vacuum may cause the thromboembolic material to attach or adhere to the distal tip; in such a case the catheter 10 or catheter body 12 and the thromboembolic material can be withdrawn from the vasculature together as a unit, for example through another catheter that surrounds the catheter 10 or catheter body 12.

As another example, the thromboembolic material may be removed from the vasculature using another technique, such as via an endovascular retrieval device delivered through the inner lumen 26 of the catheter body 12. In such a method the catheter body 12 can be inserted into the vasculature (for example using any technique disclosed herein) and the retrieval device advanced through the inner lumen 26 (or through another catheter, such as a microcatheter, inserted into the vasculature through the inner lumen 26) so that the device engages the thromboembolic material. The retrieval device and the material engaged thereby (together with any other catheter or microcatheter) can then be retracted into the inner lumen 26 and removed from the patient. Optionally, aspiration can be performed with or through the catheter body 12 during retraction of the retrieval device and thromboembolic material into the catheter body 12. The vasculature can comprise the neurovasculature, peripheral vasculature or cardiovasculature. The thromboembolic material may be located using any suitable technique, such as fluoroscopy, intravascular ultrasound or carotid Doppler imaging techniques.

Various aspects of the disclosure have been described. These and other aspects are within the scope of the following claims.

What is claimed is:

1. A catheter, comprising:
   an elongated body comprising:
      an inner liner;
      an outer jacket comprising a plurality of outer jacket segments and two or more junctions, wherein each junction of the two or more junctions is between two outer jacket segments of the plurality of outer jacket segments, and wherein each outer jacket segment of the plurality is longitudinally adjacent to another outer jacket segment of the plurality; and
      a structural support member positioned between at least a portion of the inner liner and the outer jacket,
      wherein the structural support member comprises two or more relatively high density sections interspersed with relatively low density sections,
      wherein each relatively high density section of the two or more relatively high density sections longitudinally overlaps at least one junction of the two or more junctions and at least a portion of each corresponding two outer jacket segments separated by the at least one junction, and
      wherein a first section of the structural support member having a relatively low density is radially adjacent to a first outer jacket segment, a second section of the structural support member having a relatively high density is radially adjacent to a second outer jacket segment having a lower durometer than the first outer jacket segment, and a third section of the structural support member having a relatively low density is radially adjacent to a third outer jacket segment having a lower durometer than the first and second outer jacket segments.

2. The catheter of claim 1, wherein at least two outer jacket segments of the plurality have different materials.

3. The catheter of claim 1, wherein at least two outer jacket segments of the plurality have different thicknesses.

4. The catheter of claim 3, wherein a thickness of the first outer jacket segment is less than a thickness of the second outer jacket segment.

5. The catheter of claim 3, wherein a thickness of the first outer jacket segment is greater than a thickness of the second outer jacket segment.

6. The catheter of claim 1, wherein the structural support member comprises a coiled structural support member.

7. The catheter of claim 1, wherein the structural support member comprises a braided structural support member.

8. The catheter of claim 1, wherein a surface of at least one relatively high density section of the structural support member is surface treated to increase an adhesion of the surface to at least one of the inner liner or the outer jacket.

9. The catheter of claim 1, wherein the structural support member tapers from a first diameter at a proximal end of the elongated body to a second diameter at a distal end of the elongated body.

10. A catheter, comprising:
    an elongated body comprising:
       an inner liner;
       an outer jacket comprising a plurality of outer jacket segments and two or more junctions, wherein each junction is between two outer jacket segments of the plurality of outer jacket segments, wherein each outer jacket segment of the plurality is longitudinally adjacent to another outer jacket segment of the plurality, and wherein a durometer of the outer jacket decreases from a proximal end of the elongated body to a distal end of the elongated body; and
       a structural support member positioned between at least a portion of the inner liner and the outer jacket,
       wherein the structural support member includes two or more relatively high density sections interspersed between relatively low density sections,
       wherein each relatively high density section has a density at least 25% greater than the adjacent relatively low density sections, and
       wherein each relatively high density section of the two or more relatively high density sections longitudinally overlaps at least one junction of the two or more junctions and at least a portion of each corresponding two outer jacket segments separated by the at least one junction.

11. The catheter of claim 10, wherein at least two outer jacket segments of the plurality have different materials, different durometers, or different thicknesses.

12. The catheter of claim 10, wherein at least one relatively high density section of the two or more relatively high density sections overlaps a corresponding junction by between about 5 millimeters and about 20 millimeters.

13. The catheter of claim 10, wherein a surface of at least one relatively high density section of the structural support member is surface treated to increase an adhesion of the surface to at least one of the inner liner or the outer jacket.

14. The catheter of claim 10, wherein the structural support member tapers from a first diameter at a proximal end of the elongated body to a second diameter at a distal end of the elongated body.

15. The catheter of claim 10,
wherein at least one relatively high density section is radially adjacent to a second outer jacket segment, and
wherein the adjacent relatively low density sections are radially adjacent a respective first outer jacket segment and a respective third outer jacket segment having a higher durometer than the second outer jacket segment.

16. The catheter of claim 1, wherein the at least one junction comprises a junction between materials of the two outer jacket segments.

17. A catheter, comprising:
an elongated body comprising:
an inner liner;
an outer jacket comprising a plurality of outer jacket segments and two or more junctions, wherein each junction is between two outer jacket segments of the plurality, and wherein each outer jacket segment of the plurality is longitudinally adjacent to another outer jacket segment of the plurality; and
a structural support member positioned between at least a portion of the inner liner and the outer jacket,
wherein the structural support member includes two or more relatively high density sections interspersed between relatively low density sections,
wherein each relatively high density section has a density at least 25% greater than the adjacent relatively low density sections,
wherein each relatively high density section longitudinally overlaps at least one junction of the two or more junctions and at least a portion of each of a corresponding two outer jacket segments of the at least one junction,
wherein at least one relatively high density section is radially adjacent to a second outer jacket segment,
wherein a relatively low density section is radially adjacent a first outer jacket segment,
wherein another relatively low density section is radially adjacent a third outer jacket segment, and
wherein each of the first outer jacket segment and the third outer jacket segment has a higher durometer than the second outer jacket segment.

\* \* \* \* \*